(12) United States Patent
Abrahmsohn

(10) Patent No.: US 12,059,466 B2
(45) Date of Patent: Aug. 13, 2024

(54) HYPERTONIC ANTIMICROBIAL THERAPEUTIC COMPOSITIONS

(71) Applicant: AIM Targeted Therapies, Inc., Key Biscayne, FL (US)

(72) Inventor: Glenn Abrahmsohn, Key Biscayne, FL (US)

(73) Assignee: AIM TARGETED THERAPIES, INC., Key Biscayne, FL (US)

( * ) Notice: Subject to any disclaimer, the term of this patent is extended or adjusted under 35 U.S.C. 154(b) by 358 days.

(21) Appl. No.: 17/360,968

(22) Filed: Jun. 28, 2021

(65) Prior Publication Data

US 2022/0016246 A1   Jan. 20, 2022

Related U.S. Application Data

(63) Continuation of application No. 15/021,348, filed as application No. PCT/US2014/055218 on Sep. 11, 2014, now abandoned.

(60) Provisional application No. 61/876,524, filed on Sep. 11, 2013.

(51) Int. Cl.
| | | |
|---|---|---|
| *A61K 47/02* | (2006.01) | |
| *A61K 8/19* | (2006.01) | |
| *A61K 8/20* | (2006.01) | |
| *A61K 8/22* | (2006.01) | |
| *A61K 8/40* | (2006.01) | |
| *A61K 8/43* | (2006.01) | |
| *A61K 8/46* | (2006.01) | |
| *A61K 8/49* | (2006.01) | |
| *A61K 8/86* | (2006.01) | |
| *A61K 9/00* | (2006.01) | |
| *A61K 9/06* | (2006.01) | |
| *A61K 31/155* | (2006.01) | |
| *A61K 31/18* | (2006.01) | |
| *A61K 33/40* | (2006.01) | |
| *A61K 47/16* | (2006.01) | |
| *A61K 47/26* | (2006.01) | |
| *A61K 47/32* | (2006.01) | |
| *A61K 47/42* | (2017.01) | |
| *A61L 15/18* | (2006.01) | |
| *A61L 15/20* | (2006.01) | |
| *A61L 15/44* | (2006.01) | |
| *A61L 29/08* | (2006.01) | |
| *A61L 29/10* | (2006.01) | |
| *A61L 29/16* | (2006.01) | |
| *A61L 31/08* | (2006.01) | |
| *A61L 31/16* | (2006.01) | |
| *A61Q 11/00* | (2006.01) | |
| *A61Q 17/00* | (2006.01) | |

(52) U.S. Cl.
CPC .............. *A61K 47/02* (2013.01); *A61K 8/19* (2013.01); *A61K 8/20* (2013.01); *A61K 8/22* (2013.01); *A61K 8/40* (2013.01); *A61K 8/43* (2013.01); *A61K 8/466* (2013.01); *A61K 8/498* (2013.01); *A61K 8/86* (2013.01); *A61K 9/0014* (2013.01); *A61K 9/0053* (2013.01); *A61K 9/06* (2013.01); *A61K 31/155* (2013.01); *A61K 31/18* (2013.01); *A61K 33/40* (2013.01); *A61K 47/16* (2013.01); *A61K 47/26* (2013.01); *A61K 47/32* (2013.01); *A61K 47/42* (2013.01); *A61L 15/18* (2013.01); *A61L 15/20* (2013.01); *A61L 15/44* (2013.01); *A61L 29/08* (2013.01); *A61L 29/106* (2013.01); *A61L 29/16* (2013.01); *A61L 31/08* (2013.01); *A61L 31/088* (2013.01); *A61L 31/16* (2013.01); *A61Q 11/00* (2013.01); *A61Q 17/005* (2013.01); *A61L 2300/202* (2013.01); *A61L 2300/206* (2013.01); *A61L 2300/404* (2013.01); *A61L 2300/606* (2013.01); *A61L 2420/00* (2013.01)

(58) Field of Classification Search
CPC .......... A01N 25/02; A01N 25/08; A61K 9/00; A61K 45/06; A61K 31/131; A61K 9/0014
USPC ................... 424/411; 514/642, 171
See application file for complete search history.

(56) References Cited

U.S. PATENT DOCUMENTS

| | | | |
|---|---|---|---|
| 5,192,527 A | 3/1993 | Abrahmsohn | |
| 5,209,724 A | 5/1993 | Dhaliwal et al. | |
| 5,385,738 A | 1/1995 | Yamahira et al. | |
| 5,954,680 A * | 9/1999 | Augustine | A61F 13/023 |
| | | | 607/108 |
| 6,350,781 B1 | 2/2002 | Shahinia, Jr. et al. | |
| 6,641,799 B2 | 11/2003 | Goldberg | |
| 6,921,541 B2 | 8/2005 | Grant et al. | |
| 6,926,905 B2 | 8/2005 | Grant | |
| 8,147,867 B2 | 4/2012 | Hong et al. | |
| 8,278,330 B2 | 10/2012 | Chen et al. | |

(Continued)

FOREIGN PATENT DOCUMENTS

| | | |
|---|---|---|
| JP | 2003-505415 | 2/2003 |
| JP | 2008-514640 | 5/2008 |

(Continued)

OTHER PUBLICATIONS

"Hibiclens Drug Facts,", Molnlycke Health Care, 1976, retrieved from http://dailymed.nlm.nih.gov/dailymed/fda/fdaDrugXsl.cfm?setid=4275eb53-1a7e-4a91-aac1-1085f40fac88; 7 pages.

(Continued)

*Primary Examiner* — Walter E Webb
(74) *Attorney, Agent, or Firm* — Armstrong Teasdale LLP

(57) ABSTRACT

Therapeutic compositions, primarily for topical application, and methods of making and using the composition. Pharmaceutical compositions formulated for specific forms of administration are also provided.

19 Claims, 10 Drawing Sheets

(56) References Cited

U.S. PATENT DOCUMENTS

| | | |
|---|---|---|
| 8,828,452 B2 | 9/2014 | Abrahmsohn |
| 2003/0156980 A1 | 8/2003 | Fischer et al. |
| 2003/0190373 A1 | 10/2003 | Einziger |
| 2004/0033269 A1 | 2/2004 | Hei et al. |
| 2005/0043253 A1* | 2/2005 | Cook .................. A61K 9/0043 514/35 |
| 2005/0129622 A1 | 6/2005 | Rault et al. |
| 2008/0262097 A1 | 10/2008 | Eady et al. |
| 2008/0292731 A1 | 11/2008 | Abrahmsohn |
| 2009/0208543 A1 | 8/2009 | Nathoo |
| 2009/0324662 A1 | 12/2009 | Kutsch et al. |
| 2011/0008267 A1 | 1/2011 | Arkin et al. |
| 2011/0085991 A1 | 4/2011 | Giniger |
| 2012/0082630 A1 | 4/2012 | Haught et al. |
| 2013/0089593 A1 | 4/2013 | Myntti |
| 2013/0184243 A1* | 7/2013 | Alonso ................ A61K 31/131 514/672 |
| 2016/0220675 A1 | 8/2016 | Abrahmsohn |

FOREIGN PATENT DOCUMENTS

| | | |
|---|---|---|
| JP | 2008-515882 | 5/2008 |
| JP | 2010-516815 | 5/2010 |
| WO | WO 2005/063184 | 7/2005 |
| WO | WO 2006/080398 | 8/2006 |
| WO | WO 2007/099398 | 9/2007 |
| WO | WO 2010/044679 | 4/2010 |
| WO | WO 2013/052958 | 4/2013 |
| WO | WO 2014/127367 | 8/2014 |

OTHER PUBLICATIONS

"Remington: The Science and Practice of Pharmacy," 20th ed., Lippincott, Williams & Wilkins, 2003, abstract only, 2 pages.

Ansel et al., "Pharmaceutical Dosage Forms and Drug Delivery Systems," 7th ed., Lippincott Williams & Wilkins, 1999, abstract only, 2 pages.

Carrel et al., "Cicatrization of Wounds," Laboratories of The Rockefeller Institute for Medical Research, 1917, 24 pages.

Haneke, Chloramine-T [127-65-1] and Metabolite p-Toluenesulfonamide [70-55-3], Review of Toxicological Literature, 2002, 76 pages.

Keyes, "Why use a dentifrice?", Jul. 28, 2013, retrieved from https://web.archive.org/web/20130728201711/http://mizar5.com/keyes.html, 7 pages.

Kibbe, Handbook of Pharmaceutical Excipients, 3rd edition, American Pharmaceutical Association, 2000, abstract only, 2 pages.

Rams et al. "Treatment of Juvenile Periodontitis with microbiologically modulated periodontal therapy (Keyes Technique)," Pediatric Dentistry, 1985, vol. 7(4), pp. 259-270.

International Search Report and Written Opinion for International (PCT) Patent Application No. PCT/US14/55218, mailed Dec. 16, 2014, 9 pages.

International Preliminary Report on Patentability for International (PCT) Patent Application No. PCT/US14/55218, mailed Mar. 24, 2016, 8 pages.

Official Action for Canada Patent Application No. 2,924,059, dated Oct. 13, 2017 3 pages.

Extended Search Report for European Patent Application No. 14844758.4, dated Apr. 20, 2017 7 pages.

Official Action for U.S. Appl. No. 15/021,348, mailed Jul. 29, 2016, 20 pages.

Official Action for U.S. Appl. No. 15/021,348, mailed May 19, 2017, 18 pages.

Official Action for U.S. Appl. No. 15/021,348, dated Nov. 2, 2018 10 pages.

Official Action for U.S. Appl. No. 15/021,348, dated May 16, 2019 10 pages.

Official Action for U.S. Appl. No. 15/021,348, dated Dec. 4, 2019 11 pages.

Official Action for U.S. Appl. No. 15/021,348, dated Jul. 28, 2020 14 pages.

Official Action for Australia Patent Application No. 2014318702, dated Nov. 20, 2018 4 pages.

Notice of Allowance for Canada Patent Application No. 2,924,059, dated Aug. 1, 2018 1 page.

Official Action for Canada Patent Application No. 2,924,059, dated Feb. 11, 2020 4 pages.

Official Action for Canada Patent Application No. 2,924,059, dated Sep. 4, 2020 3 pages.

Official Action for U.S. Pat. No. 2,924,059, dated Mar. 29, 2021 3 pages.

Official Action with English Translation for Japan Patent Application No. 2016-542109, dated Jun. 5, 2018 9 pages.

Official Action with English Translation for Japan Patent Application No. 2016-542109, dated May 28, 2019 12 pages.

Official Action with English Translation for Japan Patent Application No. 2016-542109, dated Jan. 12, 2021 19 pages.

Official Action with English Translation for Japan Patent Application No. 2016-542109, dated Jun. 1, 2021 5 pages.

Official Action with English Translation for Korea Patent Application No. 10-2016-7009553, dated Oct. 13, 2020 12 pages.

Official Action with English Translation for Korea Patent Application No. 10-2016-7009553, dated Apr. 12, 2021 5 pages.

Official Action with English Translation for Korea Patent Application No. 10-2016-7009553, dated Aug. 16, 2021 6 pages.

* cited by examiner

| Ingredients | | Concentration (w/w)* (*Hydrogen chloride listed as v/v) | |
| --- | --- | --- | --- |
| Class of Ingredient | Specific Ingredient | Paste | Rinse |
| Buffer | Sodium Bicarbonate | 46.8% - 55% | 6.68% - 5.5% |
| Salt | Sodium Chloride | 19.8% - 23.33% | 1.98% - 2.33% |
| Oxygen-producing compound | Hydrogen Peroxide | 0.03% - 0.9% (v/v) | 0.003% - 0.009% |
| Source of Hypochlorite | N-chloro-4-methylbenzenesulfonamide sodium salt (Chloramine-T) | 0.63% - 1.07% | 0.06% - 0.11% |
| bisbiguanide | chlorhexidine | 0.71% - 1.2% | 0.07% - 0.12% |
| poloxamer | Poloxamer 237 | 4.4% - 7.5% | 0.44% - 0.75% |
| surfactant | N,N-dimethyldodecylamine N-oxide (lauramine oxide) | 0.16% - 0.27% | 0.02% - 0.03% |
| Polyhydroxy acid | gluconolactone | 0.35% - 0.6% | 0.04% - 0.06% |
| | | pH = 9.03 +/- 0.25 | pH = 7.56 +/- 0.25 |

Fig. 1

| Ingredient | | Concentration (w/v)* (*Hydrogen chloride listed as v/v) | |
|---|---|---|---|
| Class of Ingredient | Specific Ingredient | Paste | Rinse |
| Buffer | Sodium Bicarbonate | 73% - 93.55% | 7.3% - 9.4% |
| Salt | Sodium Chloride | 30% - 39% | 3% - 3.9% |
| Oxygen-producing compound | Hydrogen Peroxide | 0.03% - 0.09% | 0.003% - 0.009% |
| Source of Hypochlorite | N-chloro-4-methylbenzenesulfonamide sodium salt (Chloramine-T) | 1.07% - 2.13% | 0.11% - 0.213% |
| bisbiguanide | chlorhexidine | 1.2% - 1.8% | 0.12% - 0.18% |
| poloxamer | Poloxamer 237 | 6.9% - 11.5% | 0.69% - 1.15% |
| surfactant | N,N-dimethyldodecylamine N-oxide (lauramine oxide) | 0.27% - 0.42% | 0.027% - 0.042% |
| Polyhydroxy acid | gluconolactone | 0.6% - 0.92% | .06% - 0.092% |
| | | pH = 9.03 +/- 0.25 | pH = 7.56 +/- 0.25 |

HYPERTONIC ANTIMICROBIAL THERAPEUTIC COMPOSITIONS

CROSS REFERENCE TO RELATED APPLICATION

This application is a continuation application of U.S. application Ser. No. 15/021,348, filed Mar. 11, 2016, which is a national stage application under 35 U.S.C. 371 of PCT Application No. PCT/US2014/055218 having an international filing date of Sep. 11, 2014, which designated the United States, which PCT application claims the benefit of priority under 35 U.S.C. § 119(e) to U.S. Provisional Patent Application Ser. No. 61/876,524, filed Sep. 11, 2013. The entire disclosures of U.S. application Ser. No. 15/021,348, PCT Application No. PCT/US2014/055218 and U.S. Provisional Application Ser. No. 61/876,524, are each incorporated herein by reference.

FIELD OF THE INVENTION

This invention relates to a composition and methods with broad antimicrobial activity against bacteria, fungi, viruses, and protozoans. The composition and methods can be used in the prevention and treatment of pathogenic processes in mammals, e.g., humans and animals, including livestock or pets, by any administration method, but is preferably applied topically.

BACKGROUND OF THE INVENTION

New regulatory measures, as well as the appearance of microbial resistance to available antibiotics, have increased the search for alternative solutions, particularly those providing effective treatment with low risk of inducing resistance.

Resistance to antibiotics has become a public health matter and has increased the cost of treatment. Therefore, the development of a composition with antimicrobial activity that does not pose resistance and toxicity problems is advantageous to animal and human health.

Thus, the inventors have developed the compositions disclosed herein to address the objectives of: providing a safe and effective composition administrable to an animal or human suffering from a condition caused by a microbial infestation or infection; minimizing side effects or tissue residues resulting from administration of the composition; providing a composition effective against a broad range of pathogens, including but not limited to, bacteria, viruses, fungi, or protozoans; and providing a composition that can be easily produced and at a reasonable cost; and all of the above with concomitant pain relief or pain reduction.

Other objectives and applications of the subject invention will become readily apparent to a person of ordinary skill in the art in view of this disclosure provided in the subject specification and drawings.

SUMMARY OF THE INVENTION

The subject invention concerns an antimicrobial composition that can be administered or topically applied to humans or other animals, providing a preventive, microbiostatic, or microbiocidal effect against a wide range of pathogenic microbes, including but not limited to, bacteria, viruses, fungi, and protozoans. Preferably, the composition is formulated as a liquid or paste useful as a topical dressing or rinse applied or administered to wounds caused by injury or surgical procedures.

Advantageously, the composition can further promote wound healing and, unexpectedly, further provides pain reduction, or pain relief, which can reduce the amount of other potentially harmful or addictive pain medication.

The composition comprises a mixture of ingredients which can be easily obtained or prepared. The composition has a long shelf life and is not known to induce resistance in the target pathogen. The composition can be applied or administered at strengths which are highly effective, yet safe to a patient in need of treatment using the composition.

A preferred embodiment of the invention comprises an antiseptic, e.g., chlorhexidine, an antimicrobial, e.g., chloramine T, and a peroxide, and one or more salts, such as sodium bicarbonate, potassium bicarbonate, sodium chloride, and the like. Chlorhexidine is commercially available as chlorhexidine gluconate (4% w/v) gluconolactone, and is often combined with ingredients such as poloxamer, isopropyl alcohol, lauramine oxide (surfactant), herbacol (fragrance), and colorant, (such as FD&C red) in water. Accordingly, a preparation of the subject invention can also comprise these ingredients.

The subject invention can be formulated as a concentrate, e.g., as a paste, gel, or ointment, or can be diluted using an aqueous or water-miscible solvent to be administered as a rinse. In either form, the composition can be administered directly to a wound area, topically or by subcutaneous injection, or can be incorporated onto or into a wound dressing material such as a bandage, patch, or suture material.

The composition of the invention can be, but is not limited to, use in the following applications:
1) Mouth rinse for antimicrobial gargle/sinus, rinse antibacterial/viral;
2) surgical rinse to decontaminate wounds;
3) surgical rinse to create pain killer in surgical sites;
4) paste (concentrate);
5) act as antimicrobial action/pre opp.wound/mouth/sinus cleanse;
6) use on washing hands/body before surgery, or for routine care;
7) act as surgical treatment to increase or potentiate healing in wounds;
8) act as an agent to create pain killer in wounds by turning local anesthetic into anesthetic bicarbonate/analgesic for post-op pain control, or inhibit pain cascade in surgical/burn wounds;
9) turn a contaminated wound into a non-contaminated wound;
) as a wound debridement;
11) to reduce or remove infections from skin, e.g., acne/rosacea;
12) insect bites, removes sting/neutralizes poison;
13) use for diabetic ulcerations/poor wound healing;
14) promote angiogenesis and tissue growth;
15) chemical/heat related burns;
16) treat resistant pathogenic microbial infections, e.g., MRSA, and the like;
17) treat traumatic injuries (war etc.), to decontaminate wounds and potentiate healing and reduce pain of trauma;
18) treat orthopedic injuries, surgeries and repairs in human or animal, including treatment and impregnation of orthopedic implants and hardware; and, 19) add to wound dressings or plugs (e.g., collagen plugs for dental extraction sites).

One aspect of the invention is a therapeutic composition comprising a chloride salt; a source of bicarbonate; a source of hypochlorite; and, an antimicrobial agent selected from biguanids, triguanides, bisbiguanides and analogs thereof; wherein the amount of the salt in the composition is sufficient to render the composition hypertonic, and wherein the composition is alkaline. In certain embodiments, the chloride salt is selected from sodium chloride and potassium chloride. In certain embodiments, the concentration of the chloride salt is at least 200 mM. In certain embodiments, the concentration of the chloride salt is in the range of about 4 molar to about 8 molar. In certain embodiments, the concentration of the chloride salt is in the range of about 5 molar to about 7 molar. In other embodiments, the concentration of the chloride salt is at least about 5 molar. In other embodiments, the concentration of the chloride salt is no greater than about 7 molar. In specific embodiments, the concentration of the chloride salt is about 6.8 molar. In certain embodiments, the concentration of the chloride salt is in the range of about 30% (w/v) to about 40% (w/v).

In certain embodiments, the source of bicarbonate is a bicarbonate salt. In specific embodiments, the bicarbonate salt is selected from the group consisting of sodium bicarbonate, calcium bicarbonate, potassium bicarbonate and ammonium bicarbonate. In certain embodiments, the concentration of the carbonate salt is in the range of about 70% to about 95% (w/v). In some embodiments, the concentration of the carbonate salt is in the range of about 8 molar to about 11 molar. In certain embodiments, the source of carbonate provides a concentration of carbonate in the range of about 4.9 molar to about 6.5 molar.

In certain embodiments, the concentration of the source of hypochlorite in the composition is about 0.5% to about 5% (w/v). In some embodiments, the concentration of the source of hypochlorite in the composition is at least 0.5% (w/v). In specific embodiments, the source of hypochlorite is tosyl-chloramide (N-chloro-tosylamide).

In some embodiments, the concentration of the antimicrobial agent in the composition is in a range of about 0.12% to about 6% (v/v). In some embodiments, the concentration of antimicrobial in the composition is in a range of about 1.2% to about 2% (v/v). In certain embodiments, the antimicrobial agent is a bisbiguanidine. In specific embodiments, the source of bisbiguanide is chlorhexidine gluconate.

In some embodiments, the therapeutic compositions additionally include a compound that provides oxygen. In these embodiments, the oxygen producing compound is peroxide. In these embodiments, the source of peroxide is selected from the group consisting of hydrogen peroxide, carbamide peroxide and sodium percarbonate. In certain embodiments, the concentration of the oxygen producing compound in the composition is in the range of about 0.1% to about 1% (v/v). In specific embodiments, the concentration of oxygen-producing compound in the composition is about 1% (v/v).

In certain embodiments, the therapeutic compositions additionally include a poloxamer. In certain embodiments, the concentration of poloxamer in the composition is in the range of about 6% to about 12% (w/v). In certain embodiments, the concentration of poloxamer in the composition is at least about 6%. In specific embodiments, the poloxamer is poloxamer 237.

In certain embodiments, the therapeutic compositions additionally include a surfactant. In certain embodiments, the surfactant is an amphoteric surfactant. In certain embodiments, the surfactant is an amine oxide. In certain embodiments, the concentration of surfactant in the composition is in the range of about 0.1% to about 1% (w/v). In certain embodiments, the concentration of surfactant in the composition is in the range of about 0.2% to about 0.5% (w/v). In specific embodiments, the surfactant is lauramine oxide (N,N-Dimethyldodecylamine N-oxide).

In certain embodiments, the therapeutic composition additionally includes a compound selected from the group consisting of an anti-microbial compound, an anti-viral compound and an anti-fungal compound.

In certain embodiments, the pH of the composition is greater than 7. In some embodiments, the pH of the composition is in the range of about 7.2 to about 7.8.

In certain embodiments, the therapeutic compositions additionally include a gluconolactone. In certain embodiments, the concentration of gluconolactone in the composition is in the range of about 0.1% to about % (w/v). In specific embodiments, the concentration of gluconolactone in the composition is at least about 0.9% (w/v).

A related aspect of the invention is a therapeutic composition including a salt selected from the group consisting of sodium chloride and potassium chloride; a source of carbonate selected from the group consisting of sodium bicarbonate, potassium bicarbonate, calcium bicarbonate and ammonium bicarbonate; a source of peroxide selected from hydrogen peroxide, carbamide peroxide and sodium percarbonate; N-chloro tosylamide; and chlorhexidine; wherein the amount of the salt in the composition is sufficient to render the composition hypertonic, and wherein the composition is alkaline.

A related aspect of the invention is a therapeutic composition including a salt selected from the group consisting of sodium chloride and potassium chloride; a source of carbonate selected from the group consisting of sodium bicarbonate, potassium bicarbonate, calcium bicarbonate and ammonium bicarbonate; a source of peroxide selected from hydrogen peroxide, carbamide peroxide and sodium percarbonate; N-chloro tosylamide; and chlorhexidine; wherein the amount of the salt in the composition is sufficient to render the composition hypertonic, and wherein the composition is alkaline.

Another aspect of the invention is a scaffolding material containing a composition of the present material. Such scaffolding material can be a biomaterial scaffold or a synthetic scaffold. Such scaffolds include, but are not limited to, collagen plugs, or equivalents, vascular wound repair devices, hemostatic dressings, patches and glues, sutures, drug delivery and in tissue engineering applications, such as, for example, scaffolding, ligament prosthetic devices and in products for long-term or bio-degradable implantation into the human body.

Another aspect of the invention is a method of treating a disease or disorder or injury in a mammal comprising administering a therapeutic composition to the mammal. In one embodiment, a therapeutic composition of this disclosure is administered to treat a wound, treat a bacterial infection, treat a viral infection, treat a fungal infection, reduce inflammation, promote angiogenesis, promote tissue growth or reduce pain.

BRIEF DESCRIPTION OF THE DRAWINGS

FIG. 2. Exemplary formulation of a paste and rinse of the present invention. Percentage of each ingredient listed as weight/weight (w/w).

FIG. 6-1 through 6-3. Treatment of facial acne using a paste of the present invention. (A) facial skin prior to treatment (frontal view); (B) facial skin after a single application of paste (front view); (C) facial skin after a single application of paste (view of right side of face); (D) facial skin after a single application of paste (view of left side of face).

FIGS. 7-1 and 7-2. Treatment of a burn resulting from hot wax using a paste of the present invention. (A) View of skin three-days after burn; (B) View of skin 8 days after burn and 5 days following treatment; (C) View of burn area one year after burn.

DETAILED DESCRIPTION OF THE INVENTION

Figure 3:
FIG. 3. Effect of a paste of the present invention on a pre-cancerous lesion of the lower lip. (A) Picture of the lesion prior to treatment; (B) paste of the present invention applied to lesion; (C) lower lip at 27 days post-treatment.
Figure 3:
Figure 3:
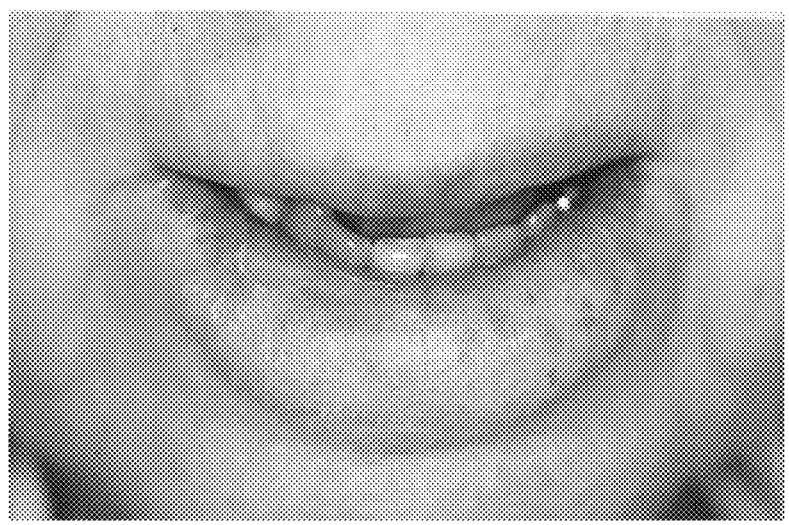

The present invention relates to compositions and formulations useful for preventing, inhibiting or ameliorating a microbial infestation or infection in humans or other animals. The composition disclosed herein exhibits preventive, microbiostatic, or microbiocidal effects against a wide range of pathogenic microbes, including but not limited to, bacteria, viruses, fungi, and protozoans. The claimed compositions and formulations are also useful for reducing inflammation and pain. In this regard, the present invention improves upon related methods disclosed by the inventors in U.S. Pat. No. 8,828,452, U.S. Patent Publication No. 2008/0292731, and International (PCT) Publication No. WO 2014/127367, the contents of which are incorporated herein by reference in their entirety. Preferably, the composition or formulation is applied or administered to wounds caused by injury or trauma, or following a surgical procedure. In various embodiments, the claimed composition or formulation can be administered or applied as a liquid or paste useful as a topical dressing or rinse, such as a dental rinse.

Advantageously, the compositions and formulations of the present invention comprise a mixture of ingredients which can be easily obtained or prepared. Before proceeding further, it should be noted that as used herein, the terms composition and formulation can be used interchangeably. Compositions of the present invention have a long shelf life and are not known to induce resistance in the target pathogen. Moreover, compositions of the present invention can be applied or administered at strengths which are highly effective, yet safe to a patient in need of treatment using the composition.

A composition or formulation of the present invention can generally be prepared by combining one or more salts that increase the tonicity of the composition, such as sodium chloride or potassium chloride, and the like, a source of carbonate, such as sodium bicarbonate or potassium bicarbonate, and the like, an antiseptic, e.g., chlorhexidine and an antimicrobial, e.g., chloramine T. In certain embodiments, a composition of the present invention may also include one or more additional ingredients selected from the group consisting of an oxygen-producing, a poloxamer, a surfactant and a polyhydroxy acid. Formulations of exemplary embodiments are summarized in the tables provided in FIG. 1 and FIG. 2.

The subject invention may preferably be formulated as a concentrate, e.g., as a paste, gel, or ointment, that can be diluted using an aqueous or water-miscible solvent to produce a liquid formulation that can be administered as a rinse or topical scrub. Preferred formulations of two different embodiments of the present invention will now be disclosed.

Paste

As noted above, a therapeutic composition of the present invention can be formulated as a paste. As used herein, paste refers to a semi-solid mixture having a consistency between a solid and a liquid. As such, it will be appreciated that pastes are made from mixing one or more solids with one or more liquids to produce a viscous composition.

In certain embodiments, a therapeutic composition of the present invention comprises at least one salt at a concentration sufficient to render the composition hypertonic. Any salt(s) capable of rendering the composition hypertonic can be used to produce a composition of the present invention, although preferred salts are chloride salts. In certain embodiments, the at least one salt is selected from the group consisting of sodium chloride and potassium chloride. In certain embodiments, the concentration of salt in the composition is at least 200 mM. In certain embodiments, a concentration of salt in a composition of the present invention is in the range of from about 4 molar to about 8 molar. As used herein, and with particular regard to concentrations, the term about means+/−5%. Thus, for example, about 4 molar refers to a range of 3.8 molar to 4.2 molar. In certain embodiments, the concentration of salt in a composition of the present invention is in the range of from about 5 molar to about 7 molar. In certain embodiments, the concentration of salt in a composition of the present invention is at least about 5 molar. In on embodiment, the concentration of salt in a composition of the present invention is no greater than about 7 molar. In certain embodiments, the concentration of salt in a composition of the present invention is about 6.8 molar.

It will be appreciated by those skilled in the art that in addition to molarity, the concentration of salt can also be measured on a weight to volume basis. In certain embodiments, the concentration of salt in a composition of the present invention is in the range of about 30% (w/v) to about 40% (w/v). In certain embodiments, the concentration of salt in a composition of the present invention is at least about 30% (w/v). In certain embodiments, the concentration of salt in a composition of the present invention is no greater than about 39% (w/v). In certain embodiments, the concentration of salt in a composition of the present invention is about 30% (w/v). In certain embodiments, the concentration of the salt in a composition of the present invention is about 35% (w/v). In certain embodiments, the concentration of the salt in a composition of the present invention is about 39% (w/v).

It will be appreciated by those skilled in the art that the concentration of salt can also be measured on a weight to weight basis. Thus, in certain embodiments, the concentration of salt in a composition of the present invention is in the range of from about 15% to about 30% (w/w/). In certain embodiments, the concentration of salt in a composition of the present invention is in the range of from about 18% to about 25% (w/w). In certain embodiments, the concentration of salt in a composition of the present invention is at least about 19% (w/w). In certain embodiments, the concentration of salt in a composition of the present invention is about 20%. In certain embodiments, the concentration of salt in a composition of the present invention is about 23%.

A therapeutic composition of the present invention further comprises a source of bicarbonate. Any source of bicarbonate can be used to produce a therapeutic composition of the present invention as along as it provides a sufficient amount of bicarbonate for the intended purpose. In certain embodiments, the source of the bicarbonate is a bicarbonate salt. In certain embodiments, the bicarbonate salt is selected from the group consisting of sodium bicarbonate, calcium bicarbonate, ammonium bicarbonate and sodium percarbonate. In certain embodiments, the concentration of bicarbonate salt in a composition of the present invention is in the range of from about 8 molar to about 11.5 molar. In certain embodiments, the concentration of bicarbonate salt in a composition of the present invention is in the range of from about 8.5 molar to about 11 molar. In certain embodiments, the concentration of bicarbonate salt in a composition of the present invention is at least 8 molar. In certain embodiments, the concentration of bicarbonate salt in a composition of the present invention is at least 11 molar. In certain embodiments, the concentration of bicarbonate in a composition of the present invention is in the range of from about 4.9 molar to about 6.5 molar. In certain embodiments, the concentration of bicarbonate in a composition of the present invention is at least 5 molar.

In certain embodiments, the concentration of bicarbonate salt in a composition of the present invention is in the range of from about 70% (w/v) to about 95% (w/v). In certain embodiments, the concentration of bicarbonate salt in a composition of the present invention is in the range of from about 73% (w/v) to about 94% (w/v). In certain embodiments, the concentration of bicarbonate salt in a composition of the present invention is at least 73% (w/v). In certain embodiments, the concentration of bicarbonate salt in a composition of the present invention is at least 93% (w/v). In certain embodiments, the concentration of bicarbonate salt in a composition of the present invention is selected from about 73% (w/v) and about 93% (w/v).

In certain embodiments, the concentration of bicarbonate salt in a composition of the present invention is in the range of from about 45% (w/w) to about 60% (w/w). In certain embodiments, the concentration of bicarbonate salt in a composition of the present invention is in the range of from about 45% (w/w) to about 55% (w/w). In certain embodiments, the concentration of bicarbonate salt in a composition of the present invention is at least 45% (w/w). In certain embodiments, the concentration of bicarbonate salt in a composition of the present invention is at least 55% (w/w). In certain embodiments, the concentration of bicarbonate salt in a composition of the present invention is selected from about 46% (w/w) and about 55% (w/w).

In certain embodiments, the ratio of bicarbonate to salt is in the range of from about 1:1.3 to about 1:3. In certain embodiments, the ratio of bicarbonate to salt is in the range of from about 1:1.3 to about 1:2.5. In certain embodiments, the ratio of bicarbonate to salt is about 1:2.3. In certain embodiments, the ratio of bicarbonate to salt is about 1:2.5.

A therapeutic composition of the present invention further comprises a source of hypochlorite. Any source of hypochlorite can be used to produce a composition of the present invention as long as it provides a sufficient amount of hypochlorite to achieve the purposes of the present invention. In a preferred embodiment, the compound used as the source of hypochlorite provides at least 0.2 grams of hypochlorite per gram of compound (e.g., 0.23 moles hypochlorite per mole of compound). In certain embodiments, the source of hypochlorite is tosylchloramide (N-chloro-tosylamide). In certain embodiments, the concentration of the source of hypochlorite is in the range of from about 0.5% (w/v) to about 3% (w/v). In certain embodiments, the concentration of the source of hypochlorite in a composition of the present invention is in the range of from about 1% (w/v) to about 2.5% (w/v). In certain embodiments, the concentration of the source of hypochlorite in a composition of the present invention is at least about 0.5% (w/v). In certain embodiments, the concentration of the source of hypochlorite in a composition of the present invention is at least about 1% (w/v). In certain embodiments, the concentration of the source of hypochlorite in a composition of the present invention is at least about 2% (w/v).

In certain embodiments, the concentration of the source of hypochlorite in a composition of the present invention is in the range of from about 0.5% (w/w) to about 3% (w/w). In certain embodiments, the concentration of the source of hypochlorite in a composition of the present invention is in the range of from about 0.5% (w/w) to about 1.5% (w/w). In certain embodiments, the concentration of the source of hypochlorite in a composition of the present invention is in the range of from about 0.6% (w/w) to about 1.5% (w/w). In certain embodiments, the concentration of the source of hypochlorite in a composition of the present invention is at least about 0.5% (w/w). In certain embodiments, the concentration of the source of hypochlorite in a composition of the present invention is at least about 1% (w/w), at least about 1.1% (w/w), at least about 1.2% (w/w), at least about 1.3% (w/w), at least about 1.4% (w/w) or at least about 1.5% (w/w).

A therapeutic composition of the present invention further comprises an antimicrobial agent selected from biguanides, triguanides, bisbiguanides and analogs thereof. Guanides, biguanides, biguanidines and triguanides are unsaturated nitrogen containing molecules that readily obtain one or more positive charges, which make them effective antimicrobial agents. The guanide, biguanide, biguanidine or triguanides, may provide bi-polar configurations of cationic and hydrophobic domains within a single molecule. Examples of guanides, biguanides, biguanidines and triguanides that are currently used as antibacterial agents include chlorhexidine and chlorohexidine salts, analogs and derivatives, such as chlorhexidine acetate, chlorhexidine gluconate and chlorhexidine hydrochloride, picloxydine, alexidine and polihexanide. Other examples of guanides, biguanides, biguanidines and triguanides that can be used in compositions of the present disclosure are chlorproguanil hydrochloride, proguanil hydrochloride, metformin hydrochloride, phenformin and buformin hydrochloride. These bi-polar cationic antimicrobial agents may also be included and used in a polymeric form, such as, guanide polymers, biguanide polymers, or polymers having side chains containing biguanide moieties or other cationic functional groups, such as benzalkonium groups or quarternium groups (e.g., quaternary amine groups). In one or more embodiments, the cationic antimicrobial polymer is a polymeric biguanide compound. When applied to a substrate, such a polymer is known to form a barrier film that can engage and disrupt a microorganism. An exemplary polymeric biguanide compound is polyhexamethylene biguanide (PHMB) salts. Other exemplary biguanide polymers include, but are not limited to, poly(hexamethylenebiguanide), poly(hexamethylenebiguanide) hydrochloride, poly(hexamethylenebiguanide) gluconate, poly(hexamethylenebiguanide) stearate, or a derivative thereof. In certain embodiments, a bisbiguanide selected from chlorhexidine (N,N-bis(4-chlorophenyl)-3,12-diimino-2,4,11,13-tetraazatetradecane diamidine) and alexidine (N-(2-ethylhexyl)-1-3-(6-{N-[3-(2-ethylhexyl) carbamimidamidomethanimidoyl]amino}hexyl)carbamimid) is included and used in the compositions of the present disclosure. In certain embodiments, the source of chlorhexidine is selected from the group consisting of chlorhexidine gluconate, chlorhexidine acetate and chlorhexidine dihydrochloride. Chlorhexidine gluconate (4% w/v) is commercially available, and is often provided in a solution combined with other ingredients such as poloxamer, isopropyl alcohol, lauramine oxide (surfactant), herbacol (fragrance), and colorant, such as FD&C red) in water. Accordingly, a preparation of the subject invention can also comprise these ingredients.

In certain embodiments, the concentration of a bisbiguanide in a composition of the present invention is in the range of from about 1% (w/v) to about 10% (w/v). In certain embodiments, the concentration of a bisbiguanide in a composition of the present invention is in the range of from about 1% (w/v) to about 6% (w/v). In certain embodiments, the concentration of a bisbiguanide in a composition of the present invention is in the range of from about 1% (w/v) to about 4% (w/v). In certain embodiments, the concentration of bisbiguanide in a composition of the present invention is in the range of from about 1.2% (w/v) % to about 2% (w/v). In certain embodiments, the concentration of a bisbiguanide in a composition of the present invention is at least about 1.2% (w/v). In certain embodiments, the concentration of a bisbiguanide in a composition of the present invention is at least about 1.8% (w/v). In certain embodiments, the concentration of a bisbiguanide in a composition of the present invention is about 1.2% (w/v) or about 1.8% (w/v).

In certain embodiments, the concentration of a bisbiguanide in a composition of the present invention is in the range of from about 0.5% (w/w) to about 5% (w/w). In certain embodiments, the concentration of a bisbiguanide in a composition of the present invention is in the range of from about 0.5% (w/w) to about 3% (w/w). In certain embodiments, the concentration of a bisbiguanide in a composition of the present invention is in the range of from about 0.5% (w/w) to about 1.5% (w/w). In certain embodiments, the concentration of a bisbiguanide in a composition of the present invention is at least about 0.7% (w/w). In certain embodiments, the concentration of a bisbiguanide in a composition of the present invention is at least about 1.2% (w/w). In certain embodiments, the concentration of a bisbiguanide in a composition of the present invention is about 0.7% (w/w) or about 1.2% (w/w).

Therapeutic compositions of the present invention can optionally comprise one or more compounds that produce oxygen. Any oxygen-producing compound can be used to produce a composition of the present invention as long as it is sufficiently stable and is able to produce a sufficient amount of oxygen to achieve the purpose of the present invention. Preferred oxygen-producing compounds are those that produce at least 60, at least 70, at least 80, at least 90 or at least 100 volumes of oxygen per volume of oxygen producing compound. For example, 1 cm$^3$ of hydrogen peroxide will produce 100 cm$^3$ of oxygen. In one embodiment the oxygen producing compound is a peroxide. In certain embodiments, the source of peroxide is selected from the group consisting of hydrogen peroxide, carbamide peroxide, benzoyl peroxide, urea peroxide, percarbamide or sodium percarbonate. In certain embodiments, the concentration of the oxygen-producing compound in a composition of the present invention is in the range of from about 0.01% (v/v) to about 0.1% (v/v). In certain embodiments, the concentration of the oxygen-producing compound in a composition of the present invention is in the range of from about 0.03% (v/v) to about 0.09% (v/v). In certain embodiments, the concentration of the oxygen-producing compound in a composition of the present invention is selected from about 0.03% (v/v), 0.06% (v/v) and 0.09% (v/v). In certain embodiments, the concentration of the oxygen-producing compound in a composition of the present invention is about 0.1% (v/v). In certain embodiments, the concentration of the oxygen-producing compound in a composition of the present invention is in the range of from about 0.001% (v/v) to about 0.01% (v/v). In certain embodiments, the concentration of the oxygen-producing compound in a composition of the present invention is in the range of from about 0.003% (v/v) to about 0.009% (v/v). In certain embodiments, the concentration of the oxygen-producing compound in a composition of the present invention is selected from about 0.003% (v/v), 0.006% (v/v) and 0.009% (v/v). In certain embodiments, the concentration of the oxygen-producing compound in a composition of the present invention is about 0.01% (v/v).

Therapeutic compositions of the present invention can optionally include a poloxamer. Poloxamers are nonionic triblock copolymers composed of a central hydrophobic chain of polypropylene oxide flanked by two hydrophilic chains of polyethylene oxide. Poloxamers are also known by the trade name PLURONIC (BASF, Florham Park, N.J.). In certain embodiments, a therapeutic composition of the present invention comprises at least one of poloxamer 108, 185, 188, 237, 238, 338, 335, and/or 407. In certain embodiments, a therapeutic composition of the present invention comprises poloxamer 237. In certain embodiments, the concentration of poloxamer in a composition of the present invention is in the range of from about 6% (w/v) to about 12% (w/v). In certain embodiments, the concentration of poloxamer in a therapeutic composition of the present invention is at least about 6% (w/v). In certain embodiments, the concentration of poloxamer in a therapeutic composition of the present invention is at least about 7% (w/v). In certain embodiments, the concentration of poloxamer in a therapeutic composition of the present invention is at least about 7.5% (w/v), at least about 8% (w/v), at least about 9% (w/v), at least about 10% (w/v) or at least about 11% (w/v). In certain embodiments, the concentration of poloxamer in a therapeutic composition of the present invention is at least about 11.5% (w/v).

In certain embodiments, the concentration of poloxamer in a composition of the present invention is in the range of from about 4% (w/w) to about 8% (w/w). In certain embodiments, the concentration of poloxamer in a therapeutic composition of the present invention is at least about 4% (w/w). In certain embodiments, the concentration of poloxamer in a therapeutic composition of the present invention is at least about 4.5% (w/w). In certain embodiments, the concentration of poloxamer in a therapeutic composition of the present invention is at least about 5% (w/w), at least about 5% (w/w), at least about 6% (w/w), at least about 7% (w/w) or at least about 7.5% (w/w). In certain embodiments, the concentration of poloxamer in a therapeutic composition of the present invention is at least about 11.5% (w/w).

In addition to the components discussed above, a therapeutic composition of the present invention can optionally include a surfactant. Any surfactant can be added to a therapeutic composition of the present invention as long as the resulting therapeutic composition is satisfactory for the purposes recited herein. For example, anionic, cationic, amphoteric and nonionic surfactants may be used in the compositions of the present disclosure. In certain embodiments, the surfactant is a non-ionic surfactant, which may include linear alcohol (C11) ethoxylate-POE-7, linear alcohol (C9-11) ethoxylate-POE-2.5, lauryl alcohol ethoxylate-POE-8, secondary alcohol ethoxylates, trideceth-2 carboxamide MEA, PEG-4 Rapeseed amide, PEG 5 Cocamide, cocamide DEA, lauramide MEA, cocamide MEA, lauramide DEA, oleamide DEA, caprylyl glucoside, myristyl glucoside, lauryl glucoside, myristyl glucoside, caprylyl glucoside, decyl glucoside, N,N-dimethyldecanamide, sophorolipid, isopropyl myristate, sopropyl palmitate, glycereth-17 cocoate, glycereth-6 cocoate, PEG/PPG-6/2 glyceryl cocoate, cetostearyl alcohol, PEG 2 cocamine, PEG 2 tallow Amine, glycereth-7 caprylate, glycereth-7 caprate, caprylic triglyceride, capric triglyceride, glyceryl oleate, glyceryl stearate, lauryl lactyl lactate, polysorbate 80 and combinations thereof. In certain embodiments, the surfactant is an amine oxide, which may include lauramine oxide, cocamidopropylamine oxide, lauryl/myristyl amidopropyl, amine oxide, tallow amine+2 eo, myristamine oxide, and combinations thereof. In specific embodiments, the surfactant is lauramine oxide (N,N-dimethyldodecylamine N-oxide). In certain embodiments, the concentration of surfactant in a composition of the present invention is in the range of from about 0.1% (w/v) to about 1% (w/v). In certain embodiments, the concentration of surfactant in a composition of the present invention is in the range of from about 0.2% (w/v) to about 0.5% (w/v). In certain embodiments, the concentration of surfactant in a composition of the present invention is at least about 0.2% (w/v). In certain embodiments, the concentration of surfactant in a composition of the present invention is about 0.27% (w/v). In certain embodiments, the concentration of surfactant in a composition of the present invention is at least about 0.4% (w/v). In certain embodiments, the concentration of surfactant in a composition of the present invention is at about 0.42% (w/v).

In certain embodiments, the concentration of surfactant in a composition of the present invention is in the range of from about 0.1% (w/w) to about 0.5% (w/w). In certain embodiments, the concentration of surfactant in a composition of the present invention is in the range of from about 0.1% (w/w) to about 0.3% (w/w). In certain embodiments, the concentration of surfactant in a composition of the present invention is in the range of from about 0.15% (w/w) to about 0.27% (w/w). In certain embodiments, the concentration of surfactant in a composition of the present invention is at least about 0.15% (w/w). In certain embodiments, the concentration of surfactant in a composition of the present invention is at least about 0.27% (w/w).

In addition to the components discussed above, a therapeutic composition of the present invention can optionally include a polyhydroxy acid selected from gactobionic acid, glucono delta-lactone (also known as gluconolactone), and blends thereof. In certain embodiments, the concentration of the polyhydroxy acid in a composition of the present invention is in the range of from about 0.5% (w/v) to about 2% (w/v). In certain embodiments, the concentration of the polyhydroxy acid in a composition of the present invention is in the range of from about 0.5% (w/v) to about 1% (w/v). In certain embodiments, the concentration of the polyhydroxy acid in a composition of the present invention is in the range of from about 0.6% (w/v) to about 0.9% (w/v). In certain embodiments, the concentration of the polyhydroxy acid in a composition of the present invention is at least about 0.5% (w/v). In certain embodiments, the concentration of the polyhydroxy acid in a composition of the present invention is at least about 0.6% (w/v). In certain embodiments, the the polyhydroxy acid of gluconolactone in a composition of the present invention is at least about 0.9% (w/v).

In certain embodiments, the concentration of the polyhydroxy acid in a composition of the present invention is in the range of from about 0.2% (w/w) to about 0.8% (w/w). In certain embodiments, the concentration of the polyhydroxy acid in a composition of the present invention is in the range of from about 0.3% (w/w) to about 0.6% (w/w). In certain embodiments, the concentration of the polyhydroxy acid in a composition of the present invention is in the range of from about 0.35% (w/w) to about 0.6% (w/w). In certain embodiments, the concentration of the polyhydroxy acid in a composition of the present invention is at least about 0.3% (w/w). In certain embodiments, the concentration of the polyhydroxy acid in a composition of the present invention is at least about 0.35% (w/w). In certain embodiments, the concentration of the polyhydroxy acid in a composition of the present invention is at least about 0.6% (w/w).

Liquid Formulation

As has been previously discussed, therapeutic compositions of the present invention can also be formulated as liquids. Such liquid formulations are useful for topical applications and as rinses. Liquid formulations of the present invention can, but need not, comprise all of the same ingredients as those disclosed for a paste formulation of the present invention, although in general, the concentrations of such ingredients are lower.

In certain embodiments, a liquid formulation of the present invention comprises a salt at a concentration sufficient to render the formulation hypertonic. In certain embodiments, the concentration of salt in a liquid formulation of the present invention is at least 200 mM. In certain embodiments, a concentration of salt in a liquid formulation of the present invention is in the range of from about 0.3 molar to about 0.8 molar. In certain embodiments, the concentration of salt in a liquid formulation of the present invention is in the range of from about 0.5 molar to about 0.7 molar. In certain embodiments, the concentration of salt in a liquid formulation of the present invention is at least about 0.5 molar. In on embodiment, the concentration of salt in a liquid formulation of the present invention is no greater than about 0.7 molar. In certain embodiments, the concentration of salt in a liquid formulation of the present invention is about 0.68 molar.

In certain embodiments, the concentration of salt in a liquid formulation of the present invention is in the range of about 3% (w/v) to about 4% (w/v). In certain embodiments, the concentration of salt in a liquid formulation of the present invention is at least about 3% (w/v). In certain embodiments, the concentration of salt in a liquid formulation of the present invention is no greater than about 4% (w/v). In certain embodiments, the concentration of salt in a liquid formulation of the present invention is about 3% (w/v). In certain embodiments, the concentration of the salt in a liquid formulation of the present invention is about 3.9% (w/v).

In certain embodiments, the concentration of salt in a liquid formulation of the present invention is in the range of from about 1.5% (w/w) to about 3% (w/w/). In certain embodiments, the concentration of salt in a liquid formulation of the present invention is in the range of from about 1.8% (w/w) to about 2.5% (w/w). In certain embodiments, the concentration of salt in a liquid formulation of the present invention is a least about 1.9% (w/w). In certain embodiments, the concentration of salt in a liquid formulation of the present invention is about 2% (w/w). In certain embodiments, the concentration of salt in a liquid formulation of the present invention is about 2.3% (w/w).

A liquid formulation of the present invention further comprises a source of bicarbonate. In certain embodiments, the source of the bicarbonate is a bicarbonate salt. In certain embodiments, the concentration of bicarbonate salt in a liquid formulation of the present invention is in the range of from about 0.8 molar to about 1.2 molar. In certain embodiments, the concentration of bicarbonate salt in a liquid formulation of the present invention is in the range of from about 0.8 molar to about 1.1 molar. In certain embodiments, the concentration of bicarbonate salt in a liquid formulation of the present invention is at least 0.8 molar. In certain embodiments, the concentration of bicarbonate salt in a liquid formulation of the present invention is at least 1.1 molar. In certain embodiments, the concentration of bicarbonate in a liquid formulation of the present invention is in the range of from about 0.5 molar to about 0.65 molar. In certain embodiments, the concentration of bicarbonate in a liquid formulation of the present invention is at least 0.5 molar.

In certain embodiments, the concentration of bicarbonate salt in a liquid formulation of the present invention is in the range of from about 7% (w/v) to about 9.5% (w/v). In certain embodiments, the concentration of bicarbonate salt in a liquid formulation of the present invention is in the range of from about 7.3% (w/v) to about 9.4% (w/v). In certain embodiments, the concentration of bicarbonate salt in a liquid formulation of the present invention is at least 7.3% (w/v). In certain embodiments, the concentration of bicarbonate salt in a liquid formulation of the present invention is at least 9.3% (w/v). In certain embodiments, the concentration of bicarbonate salt in a liquid formulation of the present invention is selected from about 7.3% (w/v) and about 9.3% (w/v).

In certain embodiments, the concentration of bicarbonate salt in a liquid formulation of the present invention is in the range of from about 4.5% (w/w) to about 6.0% (w/w). In certain embodiments, the concentration of bicarbonate salt in a liquid formulation of the present invention is in the range of from about 4.5% (w/w) to about 5.5% (w/w). In certain embodiments, the concentration of bicarbonate salt in a liquid formulation of the present invention is at least 4.5% (w/w). In certain embodiments, the concentration of bicarbonate salt in a liquid formulation of the present invention is at least 5.5% (w/w). In certain embodiments, the concentration of bicarbonate salt in a liquid formulation of the present invention is selected from about 4.6% (w/w) and about 5.5% (w/w).

In certain embodiments, the ratio of bicarbonate to salt in a liquid formulation of the present invention is in the range of from about 1:1.3 to about 1:3. In certain embodiments, the ratio of bicarbonate to salt in a liquid formulation of the present invention is in the range of from about 1:1.3 to about 1:2.5. In certain embodiments, the ratio of bicarbonate to salt in a liquid formulation of the present invention is about 1:2.3. In certain embodiments, the ratio of bicarbonate to salt in a liquid formulation of the present invention is about 1:2.5.

A liquid formulation of the present invention further comprises a source of hypochlorite. In certain embodiments, the concentration of the source of hypochlorite in a liquid formulation of the present invention is in the range of from about 0.05% (w/v) to about 0.3% (w/v). In certain embodiments, the concentration of the source of hypochlorite in a liquid formulation of the present invention is in the range of from about 0.1% (w/v) to about 0.25% (w/v). In certain embodiments, the concentration of the source of hypochlorite in a liquid formulation of the present invention is at least about 0.05% (w/v). In certain embodiments, the concentration of the source of hypochlorite in a liquid formulation of the present invention is at least about 0.1% (w/v). In certain embodiments, the concentration of the source of hypochlorite in a liquid formulation of the present invention is at least about 0.2% (w/v).

In certain embodiments, the concentration of the source of hypochlorite in a liquid formulation of the present invention is in the range of from about 0.05% (w/w) to about 0.3% (w/w). In certain embodiments, the concentration of the source of hypochlorite in a liquid formulation of the present invention is in the range of from about 0.05% (w/w) to about 0.15% (w/w). In certain embodiments, the concentration of the source of hypochlorite in a liquid formulation of the present invention is in the range of from about 0.06% (w/w) to about 0.15% (w/w). In certain embodiments, the concentration of the source of hypochlorite in a liquid formulation of the present invention is at least about 0.05% (w/w). In certain embodiments, the concentration of the source of hypochlorite in a liquid formulation of the present invention is at least about 0.1% (w/w), at least about 0.11% (w/w), at least about 0.12% (w/w), at least about 0.13% (w/w), at least about 0.14% (w/w) or at least about 0.15% (w/w).

A liquid formulation of the present invention further comprises a bisbiguanide. In certain embodiments, the concentration of bisbiguanide in a liquid formulation of the present invention is in the range of from about 0.1% (w/v) to about 1% (w/v). In certain embodiments, the concentration of bisbiguanide in a liquid formulation of the present invention is in the range of from about 0.1% (w/v) to about 0.6% (w/v). In certain embodiments, the concentration of bisbiguanide in a liquid formulation of the present invention is in the range of from about 0.1% (w/v) to about 0.4% (w/v). In certain embodiments, the concentration of bisbiguanide in a liquid formulation of the present invention is in the range of from about 0.12% (w/v) to about 0.2% (w/v). In certain embodiments, the concentration of bisbiguanide in a liquid formulation of the present invention is at least about 0.12% (w/v). In certain embodiments, the concentration of bisbiguanide in a liquid formulation of the present invention is at least about 0.18% (w/v). In certain embodiments, the concentration of bisbiguanide in a liquid formulation of the present invention is about 0.12% (w/v) or about 0.18% (w/v).

In certain embodiments, the concentration of bisbiguanide in a liquid formulation of the present invention is in the range of from about 0.05% (w/w) to about 0.5% (w/w). In certain embodiments, the concentration of bisbiguanide in a liquid formulation of the present invention is in the range of from about 0.05% (w/w) to about 0.3% (w/w). In certain embodiments, the concentration of bisbiguanide in a liquid formulation of the present invention is in the range of from about 0.05% (w/w) to about 0.15% (w/w). In certain embodiments, the concentration of bisbiguanide in a liquid formulation of the present invention is at least about 0.07% (w/w). In certain embodiments, the concentration of bisbiguanide in a liquid formulation of the present invention is at least about 0.12% (w/w). In certain embodiments, the concentration of bisbiguanide in a liquid formulation of the present invention is about 0.07% (w/w) or about 0.12% (w/w).

A liquid formulation of the present invention can optionally include a compound that produces oxygen. In one embodiment the oxygen producing compound is peroxide. In certain embodiments, the concentration of the oxygen-producing compound in a liquid formulation of the present invention is in the range of from about 0.001% (v/v) to about 0.01% (v/v). In certain embodiments, the concentration of oxygen-producing compound in a liquid formulation of the present invention is in the range of from about 0.003% (v/v) to about 0.009% (v/v). In certain embodiments, the concentration of oxygen-producing compound in a liquid formulation of the present invention is selected from about 0.003% (v/v), 0.006% (v/v) and 0.009% (v/v). In certain embodiments, the concentration of oxygen-producing compound in a liquid formulation of the present invention is about 0.01% (v/v).

Liquid formulations of the present invention can optionally include a poloxamer. In certain embodiments, the concentration of poloxamer in a liquid formulation of the present invention is in the range of from about 0.6% (w/v) to about 1.2% (w/v). In certain embodiments, the concentration of poloxamer in a liquid formulation of the present invention is at least about 0.6% (w/v). In certain embodiments, the concentration of poloxamer in a liquid formulation of the present invention is at least about 0.7% (w/v). In certain embodiments, the concentration of poloxamer in a liquid formulation of the present invention is at least about 0.75% (w/v), at least about 0.8% (w/v), at least about 0.9% (w/v), at least about 1.0% (w/v) or at least about 1.1% (w/v). In certain embodiments, the concentration of poloxamer in a liquid formulation of the present invention is at least about 1.2% (w/v).

In certain embodiments, the concentration of poloxamer in a liquid formulation of the present invention is in the range of from about 0.4% (w/w) to about 0.8% (w/w). In certain embodiments, the concentration of poloxamer in a liquid formulation of the present invention is at least about 0.4% (w/w). In certain embodiments, the concentration of poloxamer in a liquid formulation of the present invention is at least about 0.45% (w/w). In certain embodiments, the concentration of poloxamer in a liquid formulation of the present invention is at least about 0.5% (w/w), at least about 0.6% (w/w), at least about 0.7% (w/w) or at least about 0.75% (w/w). In certain embodiments, the concentration of poloxamer in a liquid formulation of the present invention is at least about 1.2% (w/w).

In addition to the components discussed above, a liquid formulation of the present invention can optionally include a surfactant. In certain embodiments, the concentration of surfactant in a liquid formulation of the present invention is in the range of from about 0.01% (w/v) to about 0.1% (w/v). In certain embodiments, the concentration of surfactant in a liquid formulation of the present invention is in the range of from about 0.02% (w/v) to about 0.05% (w/v). In certain embodiments, the concentration of surfactant in a liquid formulation of the present invention is at least about 0.02% (w/v). In certain embodiments, the concentration of surfactant in a liquid formulation of the present invention is about 0.027% (w/v). In certain embodiments, the concentration of surfactant in a liquid formulation of the present invention is at least about 0.04% (w/v).

In certain embodiments, the concentration of surfactant in a liquid formulation of the present invention is in the range of from about 0.01% (w/w) to about 0.05% (w/w). In certain embodiments, the concentration of surfactant in a liquid formulation of the present invention is in the range of from about 0.01% (w/w) to about 0.03% (w/w). In certain embodiments, the concentration of surfactant in a liquid formulation of the present invention is in the range of from about 0.015% (w/w) to about 0.027% (w/w). In certain embodiments, the concentration of surfactant in a liquid formulation of the present invention is at least about 0.015% (w/w). In certain embodiments, the concentration of surfactant in a liquid formulation of the present invention is at least about 0.027% (w/w).

In addition to the components discussed above, a liquid formulation of the present invention can optionally include a polyhydroxy acid selected from gactobionic acid, glucono delta-lactone (also known as gluconolactone), and blends thereof. In certain embodiments, the concentration of a polyhydroxy acid in a liquid formulation of the present invention is in the range of from about 0.05% (w/v) to about 0.2% (w/v). In certain embodiments, the concentration of a polyhydroxy acid in a liquid formulation of the present invention is in the range of from about 0.05% (w/v) to about 0.1% (w/v). In certain embodiments, the concentration of a polyhydroxy acid in a liquid formulation of the present invention is in the range of from about 0.06% (w/v) to about 0.09% (w/v). In certain embodiments, the concentration of a polyhydroxy acid in a liquid a formulation of the present invention is at least about 0.05% (w/v). In certain embodiments, the concentration of a polyhydroxy acid in a liquid formulation of the present invention is at least about 0.06% (w/v). In certain embodiments, the concentration of a polyhydroxy acid in a liquid formulation of the present invention is at least about 0.09% (w/v).

In certain embodiments, the concentration of a polyhydroxy acid in a liquid formulation of the present invention is in the range of from about 0.02% (w/w) to about 0.08% (w/w). In certain embodiments, the concentration of a polyhydroxy acid in a liquid formulation of the present invention is in the range of from about 0.03% (w/w) to about 0.06% (w/w). In certain embodiments, the concentration of a polyhydroxy acid in a liquid formulation of the present invention is in the range of from about 0.035% (w/w) to about 0.06% (w/w). In certain embodiments, the concentration of a polyhydroxy acid in a liquid formulation of the present invention is at least about 0.03% (w/w). In certain embodiments, the concentration of a polyhydroxy acid in a liquid formulation of the present invention is at least about 0.035% (w/w). In certain embodiments, the concentration of a polyhydroxy acid in a liquid formulation of the present invention is at least about 0.06% (w/w).

Compositions and formulations of the present invention have an alkaline pH. Without intending to being bound by theory, it is believed that alkaline formulations of the present invention prevent the formation of peroxynitrite (superoxide nitrite) from super oxide and nitric oxide. It is further believed that an alkaline formulation of the present invention neutralizes the acidic environment produced by proton release during injury. The net results of these effects is inhibition of inflammatory pathways and a switch from a catabolic state to an anabolic state. Thus, in certain embodiments, the pH of a liquid formulation of the present invention is greater than 7. In certain embodiments, the pH of a liquid formulation of the present invention is in the range of from about 7 to about 9.5. In certain embodiments, the pH of a liquid formulation of the present invention is selected from the group consisting of about 7.2, about 7.4, about 7.6 about 7.8, about 8.0, about 8.2, about 8.4, about 8.6, about 8.8, about 9.0, about 9.2 and about 9.4.

In addition to the components discussed above, compositions of the present invention can optionally include a compound selected from the group consisting of an anti-bacterial compound, an anti-viral compound, an anti-fungal compound and an anti-cancer compound. Examples of anti-bacterial agents include, but are not limited to alcohol, analides (e.g., triclocarban), bisphenols (e.g., triclosan), quaternary ammonium compounds (e.g., benzalkonium chloride) and antibiotics. Examples of anti-viral agents include, but are not limited to, acyclovir and famciclovir. Examples of anti-fungal agents include, but are not limited to, amphotericin B, clotrimazole, fluconazole, abafungin, amorolfin and caspofungin. Examples of anti-cancer agents include, but are not limited to, 5-fluorouracil, hydroxyurea, cisplatin and vinblastine.

While not intending to be limited by theory, it is contemplated that the composition, and its individual ingredients function together, symbiotically and synergistically, as described in the following table:

| INGREDIENT | PROPOSED EFFECT |
| --- | --- |
| SALT(S) | changes osmolarity from hypotonic to hypertonic solution |
| BICARBONATE OF SODA | changes pH to alkaline and neutralizes acidity; direct microbial activity; neutralizes toxins, reduces reactions to other chemicals in compositions; promotes healing; neutralizes protonic release due to inflammatory cascade; may prevent formation of superoxide nitrite and thereby reduce inflammatory cascade and thus interfere with pain pathways |
| PEROXIDE | oxygen changes environment from anaerobic to aerobic, may stimulate healing |
| SURFACTANT | lyses bacterial cell walls and so destroys bacteria |
| CHLORAMINE T | strong antimicrobial effect on bacterial/viral/fungal cell walls and DNA, so destroying the bacteria/virus/fungus while preventing formation of drug sensitivity or resistance |
| CHLORHEXIDINE GLUCONATE | strong antimicrobial effects on bacteria, viruses and fungus |

The compositions disclosed herein may be formulated in the form of a paste, a gel, a liquid (e.g. for topical or injectable administration), a putty, a foam, an ointment, a cream, a toothpaste, or in the form of an oral care composition.

Formulations for the topical or transdermal administration of compositions of this disclosure include powders, sprays, ointments, pastes, creams, lotions, gels, solutions, patches, drops and inhalants. The compositions may be mixed under sterile conditions with a pharmaceutically-acceptable carrier, and with any buffers, or propellants which may be required.

The ointments, pastes, creams and gels may contain, in addition to the composition ingredients described above, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the composition ingredients described above, excipients such as lactose, talc, silicic acid, aluminum hydroxide, calcium silicates and polyamide powder or mixtures of these substances.

Sprays can additionally contain customary propellants such as chlorofluorohydrocarbons and volatile unsubstituted hydrocarbons, such as butane and propane.

Drops, such as nose drops, may be formulated with an aqueous or nonaqueous base also comprising one or more dispersing agents, solubilizing agents or suspending agents. Liquid sprays are conveniently delivered from pressurized packs. Drops can be delivered by means of a simple dropper-capped bottle or by means of a plastic bottle adapted to deliver liquid contents drop-wise by means of a specially shaped closure.

Liquid dosage forms for administration of the compositions of this disclosure include pharmaceutically-acceptable emulsions, microemulsions, solutions, suspensions, syrups and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

By "oral care composition" is meant a product, which in the ordinary course of usage, is not intentionally swallowed for purposes of systemic administration of particular therapeutic agents, but is rather retained in the oral cavity for a time sufficient to contact substantially all of the dental surfaces and/or oral tissues for purposes of oral activity. The oral care composition may be in various forms including toothpaste, dentifrice, tooth gel, subgingival gel, mouth rinse, solutions, mousse, foam, denture care product, mouth spray, lozenge or chewable tablet. These oral care compositions of this disclosure may also be incorporated onto floss, strips or films for direct application or attachment to oral surfaces or integrated into a device or applicator such as a toothbrush or roll-ons. Such applicators may be for single or multiple use.

Preferred paste formulations are sufficiently viscous to remain in place following topical application and elute active ingredients over time. Such viscous formulations may thereby be applied adjacent to an area surrounding a wound, abrasion, infection or the like.

However, other formulations can also be used. As non-limiting examples, the subject compositions can be formulated into a powder, a dentifrice, a lozenge, a buccal adhesive patch, an oral spray, coatings that adhere to the oral cavity, chewing gum and the like. Such compositions can be formulated as is known to those of skill in the art to achieve the desired therapeutic effect(s) following topical application to skin, an open or closed wound, a mucus membrane, any portion of the oral cavity, and the like.

In some embodiments, the formulations of compositions of this disclosure include thickening or gelling agents such as polyoxyethylene/polyoxy-propylene block copolymers or carbomer polymers.

A composition utilizing carbamide peroxide, rather than hydrogen peroxide, was prepared by mixing together carbamide peroxide with the ingredients of the therapeutic compositions of this disclosure. Such formulations using the solid carbamide peroxide can be formulated as a thick gel.

In some embodiments, the formulations or compositions of this disclosure comprise a polymeric material (or polymeric precursor which forms a polymer, gel, hydrogel, or viscous fluid in situ). Exemplary polymers include polylactic acid, polyglycolic acid, poly(L-lactide) (PLLA), poly(D, L-lactide) (PLA) polyglycolic acid [polyglycolide (PGA)], poly(L-lactide-co-D,L-lactide) (PLLA/PLA), poly(L-lactide-coglycolide) (PLLA/PGA), poly(D, L-lactide-co-glycolide) (PLA/PGA), poly(glycolide-cotrimethylene carbonate) (PGA/PTMC), poly(D,L-lactide-co-caprolactone) (PLA/PCL), poly(glycolide-co-caprolactone) (PGA/PCL), poly(oxa)esters, polyethylene oxide (PEO), polydioxanone (PDS), polypropylene fumarate, poly(ethyl glutamate-co-glutamic acid), poly(tert-butyloxy-carbonylmethyl glutamate), polycaprolactone (PCL), polycaprolactone cobutylacrylate, polyhydroxybutyrate (PHBT), polyhydroxybutyrate, poly(phosphazene), poly(phosphate ester), poly(amino acid), polydepsipeptides, polyiminocarbonates, poly[(97.5% dimethyl-trimethylene carbonate)-co-(2.5% trimethylene carbonate)], poly(orthoesters), polycarbonates, polyiminocarbonates, polyphosphonates, polyethylene oxide, polyalkylene oxides, and hydroxypropylmethylcellulose.

In some embodiments, the formulations include a binder, for example polyethylene glycol (PEG). In particular embodiments, the PEG is PEG 400. The formulations disclosed herein may contain ingredients typically incorporated into oral health care compositions. Suitable ingredients can include, without limitation, abrasive polishing materials, sudsing agents, flavoring agents, humectants, binders, water and sweetening agents, in particular, high intensity sweeteners, such as sucralose, aspartame and saccharin. Abrasives which may be used in the compositions disclosed herein include alumina and hydrates thereof, such as alpha alumina trihydrate, magnesium trisilicate, magnesium carbonate, aluminosilicate, such as calcined aluminum silicate and aluminum silicate, calcium carbonate, zirconium silicate, powdered polyethylene, silica xerogels, hydrogels and aerogels and the like. Also suitable as abrasive agents are calcium pyrophosphate, insoluble sodium metaphosphate, calcium carbonate, dicalcium orthophosphate, particulate hydroxyapatite and the like.

Dyes/colorants suitable for compositions of this disclosure, such as FD & C Blue #1, FD & C Yellow #10, FD & C Red #40, and the like, may be employed in the subject formulations as well. Various other optional ingredients may also be included in the disclosed compositions, including without limitation, as preservatives, vitamins (such as vitamins C and E), anti-plaque agents such as stannous salts, copper salts, strontium salts and magnesium salts, pH adjusting agents, anti-caries agents such as calcium glycerophosphate, sodium trimetaphosphate; and anti-staining compounds such as silicone polymers, plant extracts and mixtures thereof. Additionally, polymers, particularly anionic polymers, such as polycarboxylates or polysulfonates, or polymers containing both a carboxylate and a sulfonate moiety, phosphonate polymers or polyphosphates may be included. Other optional carrier components fulfill multiple functions, for example, acting both as carriers and flavorants. Nonlimiting representative flavor oils include spearmint oil, cinnamon oil, oil of wintergreen (methyl salicylate), peppermint oil, clove oil, bay oil, anise oil, eucalyptus oil, thyme oil, cedar leaf oil, oil of nutmeg, allspice, oil of sage, mace, oil of bitter almonds, and cassia oil. Menthol, peppermint oil and eugenol are examples of carriers as well as being organic flavorants that may be used separately or in combinations in the formulation of the compositions of this disclosure.

When formulated as mouthwashes, oral rinses, throat gargles, or similar preparations, such preparations can include water/alcohol solutions, flavor components, humectants, sweeteners, sudsing agents, and colorants. These liquid formulations may include ethanol, at a level of from 0 to 60%, preferably from 5 to 30%, by weight.

In certain embodiments, the compositions of this disclosure may be formulated within an implantable material, such as a three-dimensional body defining one or more reservoirs for receiving the composition(s). Such implantable materials are preferably wettable with biological fluids. In some embodiments, the wettable materials may also be disrupted or dissolve in contact with a biological fluid.

In a further embodiment, medical devices or implants may be coated with the compositions of this disclosure. Thus, coated medical devices or implants are provided as embodiments of the invention. Such devices or implants include catheters, surgical pins, pacemaker capsules, stents, shunts, endotracheal or gastrointestinal tubes, surgical or dental implants, sutures, electrodes, dialysis devices and bandages coated with or impregnated with compositions of this disclosure.

Compositions of the present disclosure may also be introduced into a collagen plug that may be adapted to elute the composition into an opening or body cavity. In this manner, the composition may be eluted into, for example, a wound from the collagen plug. Thus, one embodiment of the invention is a collagen plug infused with a composition of this disclosure.

The compositions of this disclosure are useful in a wide variety of methods in which soft tissues and/or bone is/are altered. The methods encompass any type of tissue modifications, including tissue repair, regeneration, reconstruction and remodeling. Compositions and formulations of the present invention can also be used in tissue or implant-guided regeneration. Without being bound by theory, it is believed that the compositions and formulations aid in such repair and regeneration by inhibiting or killing infectious organisms and by reducing inflammation and pain at the site of injury or repair. These processes can encompass any type of tissue modification, including wholly internal processes as well as processes that include or affect the skin or an orifice such as the mouth or nose (e.g., the compositions described herein can be used in dental procedures). Thus, in addition to their use in conjunction with tissue fixation devices or synthetic bone substitutes or prostheses, the compositions of this disclosure may also be used in conjunction with the use of devices for attachment of orthopedic hardware (e.g., as screws for bone plates or screws to temporary secure hip stems) or in the context of reconstructive or cosmetic surgery, or repair bone, chondral and/or osteochondral defects, as often used in sports medicine implants.

In one embodiment, a composition or formulation of the present invention is used as an antiseptic mouth rinse or throat gargle. Such a rinse or gargle can be used, for example, to treat a sore throat (pharyngitis), to kill organisms that cause illness such as cold and flu, to kill organisms that cause bad breath, gingivitis, plaque, to kill organisms that cause mouth sores (e.g., herpes), to treat fungal infections of the mouth and to treat canker sores and other ulcerations of the mouth. Such a rinse or gargle can also be used to reduce inflammation in the mouth, promote growth of mouth tissue, reduce or eliminate pain in the mouth and to treat cancer and/or cancerous lesions of the mouth. One embodiment is a composition of the present invention when used as an antiseptic oral rinse or a throat gargle. One embodiment of the present invention is the use of a composition of the present invention in the preparation of a medicament for oral disinfection. One embodiment of the present invention is the use of a composition of the present invention in the preparation of a medicament for use as a throat gargle.

In certain embodiments, a composition or formulation of the present invention is used as an antiseptic rinse for sinuses. Such rinsing of the sinuses provides multiple benefits, such as; relieving nasal congestion (e.g., chronic rhinitis) and sinusitis due to infection with organisms that cause illness, such as, cold or flu; relieving sore throat pain; relieving post-nasal drip; relieving symptoms to due allergies due to mold, mildew and/or fungi; and relieving symptoms due to airborne allergens, such as, pollen, pet dandruff, dust mites, and the like. A sinus rinse can also be used for reducing general inflammation of the sinuses as well as reducing or eliminating sinus pain. One embodiment is a composition of the present invention when used as an antiseptic sinus rinse. One embodiment of the present invention is the use of a composition of the present invention in the preparation of a medicament for rinsing the sinuses. One embodiment of the present invention is the use of a composition of the present invention in the preparation of a medicament for disinfection of the sinuses.

In certain embodiments, compositions and formulations of the present invention can be used in dental procedures. In one embodiment, a formulation of the present invention is used as an anti-bacterial mouth rinse. Such a rinse can be used to treat infections of the mouth, promote angiogenesis in oral tissue, promote growth of new tissue in the mouth, reduce or eliminate mouth pain or reduce inflammation in the mouth. In one embodiment, a composition or formulation of the present invention is used to treat inflamed or damaged tissue resulting from a tooth extraction. In one embodiment, a composition or formulation of the present invention is used to treat inflamed or damaged tissue resulting from oral surgery. In addition to treating infections and reducing inflammation, such compositions and formulations can also be used to help promote angiogenesis and tissue regeneration following trauma in the mouth, tooth extractions or oral surgery. In this regard, it should be appreciated that compositions and formulations of the present invention can be applied directly to the tissue being treated or they can be applied in the form of plugs (e.g., collagen plugs,) or allografts (e.g., tissue grafts, bone grafts), that have been impregnated with a composition or formulation of the present invention. One embodiment is a composition of the present invention when used as part of a dental procedure. One embodiment of the present invention is the use of a composition of the present invention in the preparation of a medicament for use in a dental procedure.

In addition to the dental applications discussed above, the inventors have discovered that compositions and formulations of the present invention provide the surprising and unexpected benefit of reducing pain from dental procedures. Such procedures include, but are not limited to, treating periodontal disease (e.g., operculitis), periodontal scaling, root planning, curettage, tooth extractions, oral surgery, root canals, crown placements, bridge placements, and the like. In addition to the uses described above, the inventors have discovered that irrigation of an inflamed periodontal sulcus ("pocket"), resulted in shrinkage of the pocket by as much as 3-5 millimeters. Thus, in one embodiment, a composition or formulation of the present invention can be used to irrigate a periodontal sulcus. Moreover, the inventors have further discovered that, surprisingly, compositions and formulations of the present invention can be used to reduce numbness of the mouth and surrounding tissue resulting from anesthesia, without reducing the analgesic effect of the anesthesia. One embodiment is a composition of the present invention when used to reduce 1) pain or 2) numbness resulting from anesthesia. One embodiment of the present invention is the use of a composition of the present invention in the preparation of a medicament for treating pain or reducing numbness resulting from anesthesia.

While the above discussion discloses dental uses of compositions and formulations of the present invention, such compositions and formulations can also be used in surgical procedures unrelated to dental procedures. Thus, in certain embodiments, compositions and formulations of the present invention can be used in surgical procedures. In one embodiment, a composition or formulation of the present invention can be used as a general disinfectant prior to, during or after surgery. For example, a composition or formulation of the present invention can be used to disinfect hands or as a skin scrub prior to surgery. In certain embodiments, a composition or formulation of the present invention can be used to decontaminant or disinfect a surgical wound during or following surgery. For example, a paste or liquid formulation of the present invention can be used to scrub a surgical site prior to surgery. As a further example, a liquid composition of the present invention can be used to irrigate a wound or incision during surgery.

In certain embodiments, a composition or formulation of the present invention is used during surgery to reduce inflammation. In certain embodiments, a composition or formulation of the present invention is used during surgery to promote angiogenesis and/or the growth of new tissue.

In addition, the inventors have discovered that treatment of wounds using a composition or formulation of the present invention reduces or eliminates scar formation following regeneration of the wound tissue. Thus, in one embodiment, a composition or formulation of the present invention is used to reduce scar formation in a wound. Such a wound can be, for example, a surgical incision or a wound resulting from trauma, such as bullet wound, knife wound or a compound fracture. One embodiment is a composition of the present invention when used in a surgical procedure. One embodiment of the present invention is the use of a composition of the present invention in the preparation of a medicament for use in a surgical procedure.

In addition to the treatment of tissue prior to, during or after surgery, compositions and formulations of the present invention can be used to reduce pain prior to, during or following surgery. In this regard, a composition or formulation of the present invention can be administered prior to, during or following surgery.

In addition to wounds resulting from dental or surgical procedures, in certain embodiments, a composition or formulation of the present invention can be used to treat any wound. While not intending to be bound by theory, it is believed that compositions and formulations of the present invention promote wound healing by reducing or eliminating infectious organisms and promoting capillary bed formation and angiogenesis. Wounds that can be treated with compositions or formulations of the present invention include open wounds, wounds that are in the process of healing (e.g., closing) or wounds that are recently healed (e.g., closed). Such wounds can be due to any injury that results in a wound. Such wounds include, for example, cancer sores, lesions of the throat and mouth, scrapes, abrasions, evulsions, ulcerations (including diabetic ulcerations), penetrating wounds, bite wounds (human and animal), incisions, stab wounds, bullet wounds, war wounds, wounds resulting from shrapnel, wounds due to thermal burns and wounds resulting from chemical burns. In one embodiment, a composition or formulation of the present invention is used to treat an infection in a wound. Such treatment can be to prevent an infection or to reduce or eliminate an active infection. The infectious organism may or may not be resistant to antibiotics or other common compounds used to treat infections. In one embodiment, a composition or formulation of the present invention is used to reduce or eliminate scarring from a wound. In one embodiment, a composition or formulation of the present invention is used to debride a wound. In one embodiment, a composition or formulation of the present invention is used to promote angiogenesis or growth of new tissue. In one embodiment, a composition or formulation of the present invention is used to reduce inflammation in a wound. In one embodiment, a composition or formulation of the present invention is used to reduce or eliminate pain in a wound. One embodiment is a composition of the present invention when used to treat a wound. One embodiment of the present invention is the use of a composition of the present invention in the preparation of a medicament for treating a wound.

Compositions and formulations of the present invention can also be used to treat dermatological conditions. In one embodiment, a composition or formulation of the present invention is included in a facial wash. In one embodiment, a composition or formulation of the present invention is used to treat a skin infection (e.g., staph infection, chicken pox, herpes zoster virus, etc.). In one embodiment, a composition or formulation of the present invention is used to treat acne. In one embodiment, a composition or formulation of the present invention is used to treat rosacea. In one embodiment, a composition or formulation of the present invention is used to treat inflammation of the skin. In one embodiment, a composition or formulation of the present invention is used to treat a skin lesion (e.g., lump, bump, swelling, wheal, flare) resulting from an insect bite or sting. In one embodiment, a composition or formulation of the present invention is used to treat a skin lesion (e.g., lump, bump, swelling, wheal, flare) resulting from an allergic reaction (e.g., contact dermatitis). One embodiment is a composition of the present invention when used to treat a dermatological condition. One embodiment of the present invention is the use of a composition of the present invention in the preparation of a medicament for treating a dermatological condition.

In addition to the uses described above, the inventors have discovered that compositions and formulations of the present invention can be used to treat lesions resulting from, or otherwise relating to, tumors. Such lesions can be pre-cancerous lesions, or they can be lesions that result from direct damage by tumor cells, or damage resulting from an immune response to the growth of tumor cells. Such lesions may also be due to tissue damage resulting from treatment of a tumor with an anti-tumor agent such as a chemotherapeutic agent. In one embodiment, a composition of the present invention is used to treat a pre-cancerous lesion. In one embodiment, a composition of the present invention is used to treat a cancerous lesion. In one embodiment, a composition of the present invention is used to treat a tumor or cancer-related lesion. In one embodiment, a composition of the present invention is used to reduce inflammation resulting from a cancer or a tumor. In one embodiment, a composition of the present invention is used to reduce pain resulting from a cancer or a tumor. One embodiment is a composition of the present invention when used to treat a lesion related to cancer or a tumor. One embodiment of the present invention is the use of a composition of the present invention in the preparation of a medicament for treating a lesion related to cancer or a tumor.

In certain embodiments, a composition or formulation of the present invention is used to treat a cancer or tumor. Such cancers or tumors can be benign or malignant. Such cancers or tumors can be systemic or localized. In a preferred embodiment, the tumor or cancer being treated is localized. Compositions and formulations of the present invention can be used to treat ay tumor although preferred tumors are those to which a composition or formulation of the present invention can be applied directly. In one embodiment, a composition or formulation of the present invention is used to inhibit the growth of tumor cells. In one embodiment, a composition or formulation of the present invention is used to kill tumor cells. One embodiment is a composition of the present invention when used to treat a cancer or a tumor. One embodiment of the present invention is the use of a composition of the present invention in the preparation of a medicament for treating a cancer or a tumor.

In one embodiment, a composition or formulation of the present invention is used to prepare a biomaterial scaffold product. Biomaterial 'scaffold' products of various materials, shapes and sizes are well known for use in a variety of medical applications such as wound closure systems, including vascular wound repair devices, hemostatic dressings, patches and glues, sutures, drug delivery and in tissue engineering applications, such as, for example, scaffolding, ligament prosthetic devices and in products for long-term or bio-degradable implantation into the human body. The scaffold serves as both a physical support and an adhesive substrate during implantation. The ideal bioabsorbable scaffold has sufficient mechanical properties to perform its primary function but over time the implant should ideally get replaced by natural tissue that is surrounding the implant. In certain embodiments the material releases compounds that aid the repair and replacement process. Tissue engineered scaffolds for use in such applications are well known and may include, for example, woven or non-woven networks of biocompatible fibers, biocompatible and restorable polymers or sponges or microspheres, synthetic or recovered bone fragments, hydrogels, foams, silks, and the like.

Thus, certain embodiments of the invention include such biomaterials containing therapeutic compositions of the present disclosure. To form these materials, the biomaterial is mixed with a therapeutic agent prior to forming the material or loaded into, or onto, the material after it is formed (i.e., the biomaterial is impregnated, soaked in or coated with, a composition of this disclosure after formation). The therapeutic compositions, as applied to or present in these biomaterials may be present as a liquid, a finely divided solid, a paste, or any other appropriate physical form that is compatible with and does not adversely affect the performance of the biomaterial.

The biomaterial-therapeutic composition combinations of this embodiment may be prepared for storage under conditions suitable for the preservation of activity of the composition as well as maintaining the integrity of the biomaterial, and are typically suitable for storage at ambient or refrigerated temperatures.

Compositions and formulations of the present invention can be administered directly to a wound area, topically as a rinse, drench, or ointment, or by subcutaneous or intralesional injection. Similarly, these compositions can be incorporated onto or into wound dressing materials such as a bandage, patch, collagen plug, or suture material.

When employed as pharmaceuticals, the compositions of the present disclosure are administered in the form of pharmaceutical formulations. These formulations can be administered by a variety of routes including oral, rectal, topical, subcutaneous, intramuscular, and intranasal. Preferably, these formulations are administered topically when used to treat wounds or infections. Such formulations are prepared in a manner well known in the pharmaceutical art and comprise at least one composition of the present disclosure.

Thus, other aspects of the invention include methods of using of a composition of this disclosure in the preparation of a medicament for the treatment of a mammal in need of such treatment suffering a disease or disorder as described above. This aspect of the invention includes compositions of this disclosure for use in the treatment of a mammal in need of such treatment suffering a disease or disorder as described above. In certain embodiments, methods of treatment according to this invention include treatment of a mammal in need of such treatment suffering a disease or disorder as described above comprising administering an effective amount of a composition of this disclosure to an individual in need thereof.

EXAMPLES

The following examples are put forth so as to provide those of ordinary skill in the art with a complete disclosure and description of how to make and use the embodiments, and are not intended to limit the scope of what the inventors regard as their invention nor are they intended to represent that the experiments below are all or the only experiments performed. Efforts have been made to ensure accuracy with respect to numbers used (e.g. amounts, concentrations, times, etc.) but some experimental errors and deviations should be accounted for. Standard medical and scientific abbreviations are used.

Example 1

This Example illustrates the preparation of a paste of the present invention.

A stock solution of chloramine-T was first prepared by adding 47.5 ounces (1204.854 grams) to one gallon of sterile water in a dark brown (light-resistant) container and the resulting solution mixed thoroughly. The solution was then filtered through a micropore filter into a second light-resistant (dark brown) container. The solution was then aliquoted into light-resistant bottles, with each aliquot containing 10-20 milliliters (mls).

93.553 grams of sodium bicarbonate were weighed out and added to 39.689 grams of sodium chloride in a sterile mixing bowl. To this dry mixture was added 3-6 mls of the chloramines-T stock solution, 1 milliliter (ml) of 3% hydrogen peroxide, and 30 milliliters of a solution containing 3.63% (w/v) chlorhexidine gluconate, 3.64% (v/v) isopropyl alcohol, 25.1% (w/v) poloxamer 237, 0.89%-0.99% (w/v) lauramine oxide), 2.14% (w/v) gluconolactone and 36.1 mg/L FD&C Red 40. The ingredients were mixed with a wooden ladle until the mixture was fully incorporated.

The resulting paste had a total volume of approximately 100 mls, and a weight of 6 ounces (170.01 grams). The mixture was stored in a tightly sealed, sterile, light-impervious porcelain container having a lid with a rubber seal.

A liquid rinse was made from the paste by adding 5 ml of paste to 50 ml of sterile water.

Example 2

Effect of a paste of the present invention on a pre-cancerous lesion of the lower lip of a patient treated iatrogenically with 5-Fluorouracil). The patient, an avid golfer with a lifetime of sun exposure, was on a Coumadin anti-coagulation regime. The 5FU, had caused severe desquamation of the lip and uncontrollable bleeding (FIG. 3A). A paste made according to Example 1 was applied to the lesion daily (or bi-daily) for 10 minutes per treatment (FIG. 3B), followed by application of vitamin E. After 27 days of treatment, the lesion was completely healed (FIG. 3C).

Example 3

Figure 4:
FIG. 4. Effect treating an oral pre-cancer with a composition of the present invention. (A) Picture of the lesions on the tongue prior to treatment; (B) view of the tongue at 27 days post-treatment; (C) at 27 days post-treatment.
Figure 4:
Figure 4:
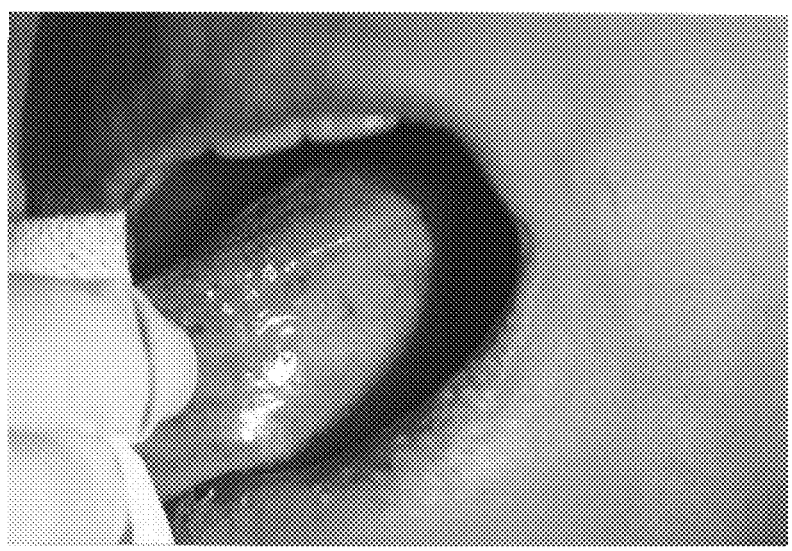

Effect of a paste of the present invention on a diagnosed pre-cancerous lesion of the mid lateral aspect of the tongue. A 72-year-old female showing confirmation of cancer with a second diagnostic vizilite test for cancer (FIG. 4A). A paste made as described in Example 1 was applied to the lesion for ten minutes daily, or on alternative days, for 27 day, after which the lesion was treated with Vitamin E oil. This treatment resulted in complete remission of the lesion together with a loss of the hyperkeratotic tissue (FIG. 4C).

Example 4

Figure 5:
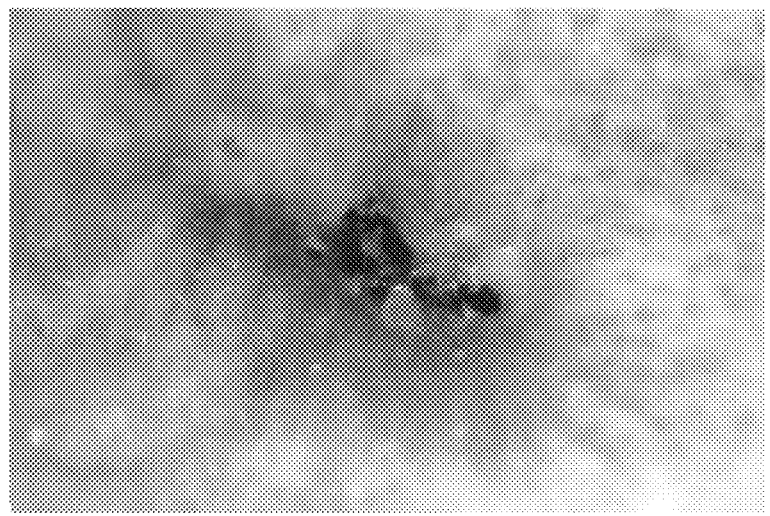
FIG. 5. Treatment of scar tissue containing antibiotic-resistant bacteria using a paste of the present invention. (A) View of scar tissue lesion prior to treatment; (B) View of scar tissue lesion after 8 days of treatment; (C)) View of scar tissue lesion after finishing of treatment.
Figure 5:
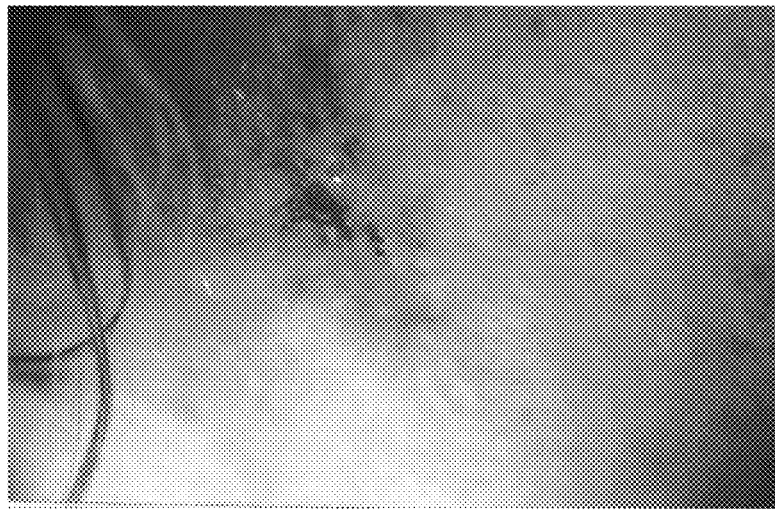
Figure 5:

Treatment of scar tissue containing antibiotic resistant bacteria (FIG. 5A). A 67-year-old, white female, presented with a persistently draining sinus and fistula, following facial surgery. Scar tissue from the surgery was infected with a drug-resistant bacteria. A high-dosages paste, prepared as described in Example 1 and using 6 mls of Chloramine-T, was applied to the scar tissue, 20 minutes per application, for 45 days. Following application of the paste, the scar tissue was then treated with vitamin E oil. The above-described treatments resulted in closure of the fistula and complete healing of the wound (FIG. 5C).

Example 5

Treatment of facial acne using paste of the present invention.

Figures 1, 6:
Figures 2, 6:
Figure 6:
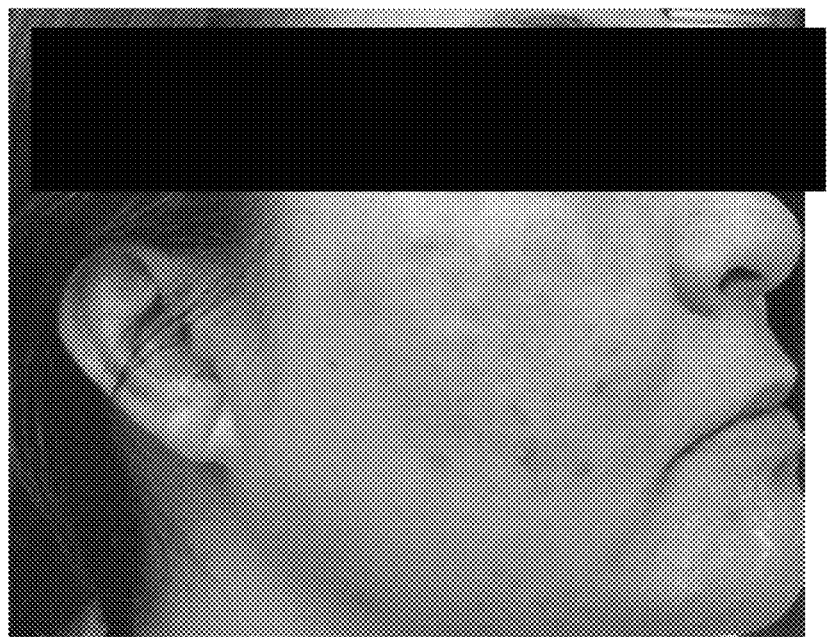
Figure 3:

A 44 year old Hispanic female presented with severe long term acne vulgaris on her face (FIG. 6-1). Paste prepared as described in Example 1 was applied once to the acne lesions for 10 minutes. The result of this single application is shown in FIGS. 6B through 6D.

Example 6

Treatment of Third Degree Burn

Figure 7:
Figure 1:
FIG. 1. Exemplary formulation of a paste and rinse of the present invention. Percentage of each ingredient listed as weight/volume (w/v) (with the exception of hydrogen peroxide).
Figures 2, 7:
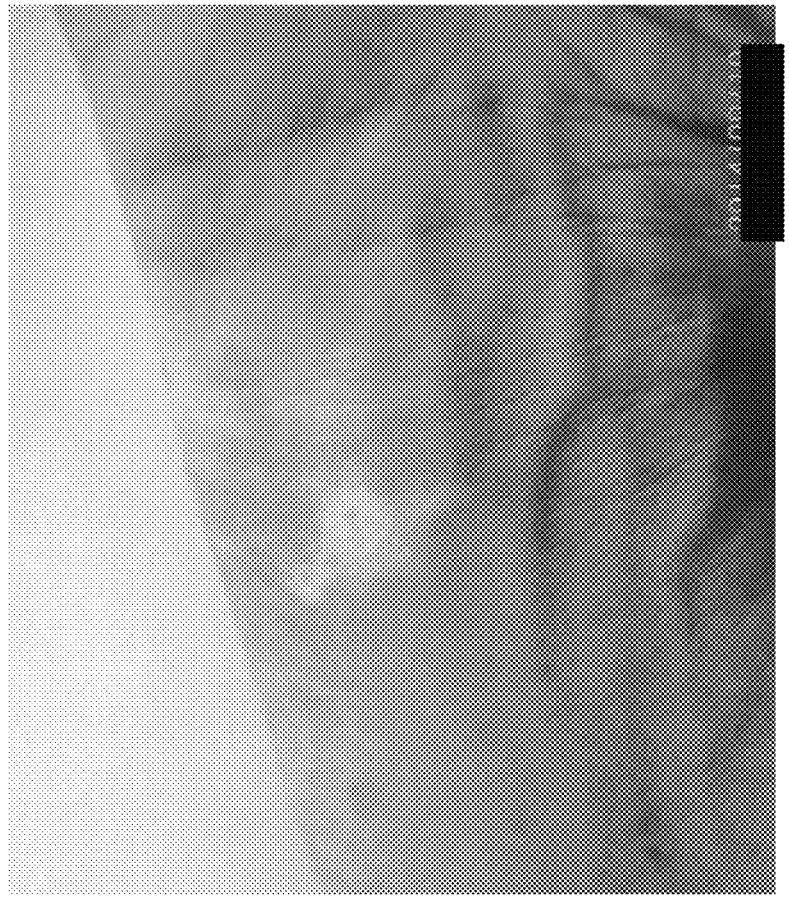

A 66 year old white female presented with a third degree burn resulting from contact with hot wax. (FIG. 7A). Past, prepared according to Example 1 was applied b.i.d. for two weeks. Each application of paste was followed by an application of vitamin E oil. This treatment regime resulted in complete healing of the burn with minimal scarring. (FIG. 7C)

Example 7

A retrospective study of 50 consecutive oral surgery patients (26 males/24 females, all signing consents) were treated with either the rinse or the paste or a collagen plug impregnated with the paste, and were followed for post-operative complications, to include pain indexing. The objective of this study is to observe the pain response and complications to conventional surgical therapy, if any, of a composition of the subject invention. The study was conducted at The Dental Connection in Key Biscayne, Florida In this retrospective study of 50 consecutive dental surgical patients, patients were monitored for the effects of a composition of the subject invention, prepared as a paste or rinse, and administered during surgery or for post-surgical care. Patients aged 18 to 96 were given either a rinse, paste and/or a collagen plug impregnated with the composition to the surgical site, and were scored for post-operative pain. The testing process was progressive and un-blinded.

In the early stages of the study, a rinse to the wound or area was applied, later a rinse and paste and finally an impregnated sterile collagen plug placed into the wound and left in situ, sutured in position. Patients were assessed for pain the first day and then each day, for up to 2 days. Each patient was asked to score pain as: 0=no pain, 1=mild pain, 2=moderate pain, and 3=severe pain. Pain killers were prescribed, Ibuprofen 800 mgs. Q-6 hourly, or Percocet #5 325 mgs.

Patients were instructed to keep track of the amount of pain (using the designated 0-1-2-3 scale), the amount of pain killers taken and when.

Patients were also instructed to take 800 mgs of Ibuprofen or Ibuprofen as soon after surgery as possible and that, if pain was not controlled by these tablets, then to take 1 Percocet #5 325 mgs Q 2-3 hourly, until the pain was under control. Antibiotics were given routinely the night prior to surgery and patients were asked to continue for 5 days. Also probiotics (Jarro-dophilus or live yogurt) were prescribed to reduce the untoward effects of the antibiotic therapy. Vitamin C 500 mgs. t.i.d. was also recommended to be taken 3 times per day for three weeks with meals.

Cases involving the sinus and placement of implants were explored. So too were large cysts solitary, apical and periodontal lesions, caused by chronic infections. Using socket preservation techniques then bone augmentation using human or animal (cow) freeze dried mineralized bone, plus judicial use of membranes to re-grow alveolar bone, it was possible to place implants. Wounds and surgical sites, infected and non-infected were used to put this substance through its paces. All surgical techniques used were standard accepted procedures. Some patients received oral sedation using Triazolam 0.25 mgs or Diazepam 10 mgs at the start of their procedures assisted with nitrous oxide and oxygen through a nose mask.

Summary of Results—50 patients: 26 males, 24 females (mean age of men 44.8/women 51.9). The results of those patients male and female who had simple extractions and who had rinse/paste placed in the wounds post-operatively had virtually no pain post-operatively, took very few pain killers and complained of very little post-operative pain.

Those male patients who had Collaplug impregnated with rinse/paste scored slightly higher on the pain index at 1.3 the first day with the Collaplug versus 0.75 without the Collaplug and the women with the Collaplug had 0.5 pain index on average and without the Collaplug 0.75 pain index. Both male and female scoring at the minimum pain level was remarkable for a first day post-operative pain score.

All patients both male and female complained of a pain index of 0.5 day two with or without the Collaplug. Regarding the group of males who had simple single extractions, teeth #15, #7, #8, #16 and who had the rinse placed into the wounds post operatively and the paste placed to the closed wounds, virtually no pain killers were used by this group and the members experienced little to no post-operative pain.

| Male Average Pain | Female Average Pain |
|---|---|
| $1^{st}$ Day = 0.68 | $1^{st}$ Day = 0.875 |
| $2^{nd}$ Day = 0.36 | $2^{nd}$ Day = 0.3 |

Methods
Oral Surgery—Periodontics—Implants—Retrospective Study (Pain Scale 0=None, 1=Mild, 2=Moderate, 3=Extreme)
Males (n=26)—Average Age=44.8

A. Patient 044—66 y/o Male
Problem: Fractured bridge #12 to #14-#12 cyst 10 mm×10 mm—cyst had perforated sinus—heavy ETOH—bruxist—taking Plavix
First procedure—patient placed on Augmentin prior to surgery. Cut off bridge #14, raised flap #11 to #14. Sinus lift 6 mm window #12 site Bio-Oss, Bone & Bio-Gide membrane into sinus, Collatape to entry, freeze dried mineralized bone to #12 after cyst enucleated, socket preservation, Collatape impregnated with paste to cover membrane.
Second procedure—patient placed on Augmentin prior to surgery—12-15 incision graft of attached gingivae—Straumann implant placed to #12 site 4.8×12 mm R/N and #14 site 4.8×12 mm W/N—#14 root augmented with Tetracycline, freeze dried mineralized bone and Bio-Oss—successful results.
Paste and rinse post-operative daily 3×/day for 4 days for each procedure—no complications reported.
  Pain Score: $1^{st}$ Day=1—One ibuprofen 800 mgs, all day
    $2^{nd}$ Day=1—One Percocet 325 mgs (Oxycodeine)
  B. Patient 051—67 y/o Male
Problem: bruxist—overactive Thyroid condition—needs implants
First procedure—3i implants placed to #19 site 5/6×13 mm and to #20 site 4/5×13 mm—no complications reported.
  Pain Score: $1^{st}$ Day=0
    $2^{nd}$ Day=0
Second procedure—Straumann implant placed to #2 site 4.8×10 mm W/N SL Active Ti—no complications.
  Pain Score: $1^{st}$ Day=0
    $2^{nd}$ Day=0
  C. Patient 038—47 y/o Male
Problem: #18 severe infection, tooth fractured with large cyst 13 mm×15 mm close to Inferior Dental Nerve—High ETOH
Procedure—enucleated cyst—osteograft (cow bone) placed—Collaplug with paste and rinse—placed on antibiotics—no complications, minimal pain
  Pain Score: $1^{st}$ Day=1.5
    $2^{nd}$ Day=0
  D. Patient 042—19 y/o Male
Problem: Multiple extractions
Surgical extraction of teeth #B, #C, #I, #5, #R, #Q, #N, #M, #L, #K
  Pain Score: $1^{st}$ Day=1
    $2^{nd}$ Day=1
  E. Patient 034—47 y/o Male Problem: Site regeneration then needs implants—lower right first—lower left second—multiple treatment surgeries—severe infections and severe decay—bruxist—smoker, one P/P/D—ETOH First procedure—to each side, socket preservation—site regeneration—#30, #29—freeze dried mineralized bone Second procedure—enucleated cyst 13 mm×15 mm on #19, #18 site—freeze dried mineralized bone.

Third procedure—lower right, Straumann implant placed to #30 site 6.8×12 mm W/N—freeze dried mineralized bone—Straumann implant placed to #28 site 4.1×12 mm—freeze dried mineralized bone, $CaSO_4$.

Fourth procedure—lower left, Straumann implants placed to #18, #19 sites 4.8×12 mm SP—3 bottles ½ gm each freeze of dried mineralized bone, $CaSO_4$ plus membrane—antibiotics used Clindamycin 300 mgs, Amoxicillin 500 mgs for 7 days, paste and Vitamin E—no complications Post op: multiple visits paste and vitamin E—had a crack on left lip it had crusted after surgery and caused pain Pain Score: (from surgical sites) $1^{st}$ Day=0
    $2^{nd}$ Day=0

F. Patient 025—76 y/o Male

Problem: #15 super erupted needed extraction—bipolar—no pain threshold

Procedure—surgical extraction of tooth #15—Collaplug impregnated with paste—no antibiotic needed—no complications Post-op: Ibuprofen 800 mgs stat—5:00 p.m. 2 Extra-Strength Tylenol—8:00 p.m. Ibuprofen 800 mgs.

Pain Score: $1^{st}$ Day=0.5 (virtually no pain)
    $2^{nd}$ Day=−1

G. Patient 037—70 y/o Male

Problem: needs multiple implants and sinus grafts—long history of sinus infections (since 14 years of age)—poor health—multiple medications—severe clencher/bruxist—severe decay—cracked tooth syndrome—high BP—Diabetes—PSAIII First procedure—#30 immediate extraction and placement of Straumann implant 4.8 mm bone level—paste and irrigation and placement of freeze dried mineralized bone.

Average Pain index $1^{st}$ Day=1.5—1 Ibuprofen, 2 Tylenol #3, Ibuprofen

Pain index $2^{nd}$ Day=0

Second procedure—#14 extracted, sinus perforation repaired with Biomend—socket preservation ½ gm freeze dried mineralized bone—Clindamycin 300 mgs three times a day for 5 days plus Jarro-dophilus probiotics Post-op: 1 Ibuprofen 800 mgs stat Post-op complication: dry socket, placed on vitamin C 1000 mgs three times a day for three weeks—good resolution Pain index $1^{st}$ Day=1-2 Tylenol #3, Ibuprofen before bed, fever broke at 1:30 a.m.

$2^{nd}$ Day=1—1 Ibuprofen 800 mgs

Third procedure:—#15 Sinus tap and Straumann implant, Bio-Oss, 4.8×10 mm B/L

Pain index $1^{st}$ Day=2.5
    $2^{nd}$ Day=2

Fourth procedure—#14 extraction and immediate placement of Straumann implant 4.8×10 mm TE—perforation of sinus repaired with paste plus Collaplug, Collatape, freeze dried mineralized bone and $CaSo_4$ Post-op—placed on Vitamin C 1500 mgs three times per day, paste applied to mouth and nose Pain index $1^{st}$ Day=1.
    $2^{nd}$ Day=0

Problem: against medical advice patient decided to leave town for one month and returned with raging sinus infection and suppurating pus. Placed on Clindamycin 300 mgs and metronidazole 500 mgs t.i.d.×10 days—rinse, paste to mouth and nose (6 minutes) daily for 10 days—a bad situation with a successful conclusion.

3 fractured—palatal root caries and separated from crown—wants to delay implant surgery as has many serious commitments Fifth procedure—surgical removal of roots—severe perio defect on #2—socket preservation with MinerOss, Bio-Gide membrane and Collatape with paste—antibiotic Clindamycin 150 mgs three times a day for 10 days and metronidazole 500 mgs three times a day for 10 days—paste for 10 minutes, mouth rinse—Success!!

Pain index $1^{st}$ Day=0
    $2^{nd}$ Day=0

Sixth procedure—Extraction #4 and immediate placement of Straumann implants to #3 site 4.8×10 mm W/N TE and #4 site 4.1×10 mm R/N TE with Caldwell Luc sinus lift, Bio-Guide, Bio-Oss. Tear to membrane repaired with Bio-Mend—paste and Vitamin E—stopped antibiotics due to stomach even though taking probiotics—no complications this time.

Pain index—1st day=0—1 Ibuprofen 800 mgs
    2nd day=1
    $3^{rd}$ day=less than 1
    $4^{th}$ day=less than 1
        Aggregate Pain Score: $1^{st}$ Day=1.2
        $2^{nd}$ Day=0.2

H. Patient 026—79 y/o Male

Problem: needs tooth #8 extracted and immediate partial placed—no pain threshold Procedure—uncomplicated surgical extraction tooth #8 and placement of immediate partial—Collaplug with paste and irrigation with rinse Pain Score: 1st Day=1
    $2^{nd}$ Day=2

I. Patient 035—80 y/o Male

Problem: #18, #19 failed implants—difficult case—heart valve replacement—Coumadin—bruxist—very strong bite First procedure—tried to salvage implants in #20, #21 sites, flap Tetracycline 2 minutes, paste and freeze dried mineralized bone with $CaSo4$ and membrane Pain index—$1^{st}$ Day=0
    $2^{nd}$ Day=0

Second procedure—removed failed implants to #20, #21 site—Amoxicillin, freeze dried mineralized bone, Bio-Mend membrane for socket preservation Pain index—$1^{st}$ Day=0
    $2^{nd}$ Day=0

Third procedure—#4 extracted and augmented with freeze dried mineralized bone along with immediate placement of Straumann implant to site #4 4.8×12 mm B/L Pain index—$1^{st}$ Day=0
    $2^{nd}$ Day=0

Fourth procedure—#21 site Tetracycline 2 minutes—freeze dried mineralized bone and Bio-Mend—Straumann implant placed to site #21 4.8×12 mm, wound irrigated with paste, Amoxicillin, 2 extra-strength Tylenol.

Pain index—$1^{st}$ Day=0
    $2^{nd}$ Day=0

Fifth procedure—#21 implant uncovered—removed granulation

Pain index—$1^{st}$ Day=0
$2^{nd}$ Day=0

Sixth procedure—#14, #13 extractions and immediate placement of Straumann implants #14, 4.8×10 mm TE—#13

4.1×12 mm TE—Augmentin—sinus perforation, rinse and paste to wounds, freeze dried mineralized bone—no complications Pain index—1$^{st}$ Day=0 Aggregate Pain Score: 1$^{st}$ Day=0
2$^{nd}$ Day=0 2$^{nd}$ Day=0

J. Patient 047—18 y/o Male

Problem: 4 very difficult impacted wisdom teeth (10/10 difficulty)—mesio-angular low involving nerve in the lower left side worst—upper #1, #16 high hooked roots and splayed.

Procedure—surgical extraction of #1, #16, #17, #32—2 Extra-Strength Tylenol one hour prior to appointment—Collaplug with rinse—photos taken—daily rinses Aug. 6, 2010 through Aug. 13, 2010.

Pain Score: 1$^{st}$ Day=2
2$^{nd}$ Day=1

K. Patient 050—62 y/o Male

Problem: #8 cyst 8 mm×7 mm Procedure—apicectomy #8—freeze dried mineralized bone—Tetracycline with CaSo4 membrane—paste and rinse to the wound—no complications Pain Score: 1$^{st}$ Day=0
2$^{nd}$ Day=0

L. Patient 033—90 y/o Male

First procedure—2 Extra-Strength Tylenol prior to procedure—surgical extractions of teeth #19, #20, #22 and immediate placement of Straumann implants to #19 site implant 12 mm W/N Plus, to #20 site 10 mm R/N Plus, to #22 site 12 mm R/N Plus—wounds irrigated with rinse—paste applied to wounds along with freeze dried mineralized bone—very hard bone—played tennis day after procedure.

Pain Score 1$^{st}$ Day=3
2$^{nd}$ Day=2

Second procedure—#9 surgical extraction and immediate placement of implant—no complications Pain Score 1$^{st}$ Day=0
2$^{nd}$ Day=0

Third procedure—#30 extraction and immediate placement of Straumann implant 4.8×10 mm plus freeze dried mineralized bone with paste and rinse—no complications Pain Score: 1$^{st}$ Day=0
2$^{nd}$ Day=0

M. Patient 041—19 y/o Male

Problem: #1, #16, #17, #32 deep impacted wisdom teeth (9/10 difficulty)—roots partially formed—uppers high Procedure—Amoxicillin—2 Extra Strength Tylenol—#1, #16, #17, #32 extracted—Collaplugs plus paste—rinse to wounds after extractions—no complications Pain Score: 1$^{st}$ Day=1
2$^{nd}$ Day=1

N. Patient 048—39 y/o Male

Problem: Severe bone loss #14—sinus perforation—Marfans Syndrome—anti-coagulants Procedure—#14 socket preservation—augmentation—Collatape paste and rinse, freeze dried mineralized bone, hypoglycemic, sugar given. Rinse to site, mouth and nose. Augmentin 875 mgs for 6 days, probiotics—no complications Pain Score: 1$^{st}$ Day=1
2$^{nd}$ Day=0

O. Patient 040—18 y/o Male

Problem: wisdom teeth 7.5 out of 10 difficulty

Procedure—#1, 16, 17, 32 surgical extraction—Amoxicillin—2 extra-strength Tylenol one hour prior to surgery—sedation—Collaplug plus paste/rinse—paste to close wounds Pain Score: 1$^{st}$ Day=1.5
2$^{nd}$ Day=0

P. Patient 046—18 y/o Male

Problem: Wisdom teeth—#16 palatal very high=9/10 difficulty—#1, #17, #32=7/10 difficulty Procedure: #1, 16, 17, 32 surgical extraction—2 extra-strength Tylenol One hour prior to surgery—Collaplug plus paste into wounds—uppers no Collaplug only rinses with paste—all sockets irrigated with paste—no complications Pain Score: 1$^{st}$ Day=2
2$^{nd}$ Day=1.5

Q. Patient 027—35 y/o Male

Problem: #16 super erupted

Procedure—surgical extraction #16—2 Extra strength Tylenol one hour prior to surgery—Collaplug plus paste—no complications Pain Score: 1$^{st}$ Day=0
2$^{nd}$ Day=0

R. Patient 043—49 y/o Male—Heavy Smoker—Over Weight—High Stress Lifestyle—Constantly Having to Fly Because of Business Commitments—Poor Compliance Problem: very difficult wisdom teeth (12/10)—high risk nerve injury—needs++bone removal—deep impaction Procedure—#17, #32 surgical extraction—Collaplug—no paste—Amoxicillin—2 extra-strength Tylenol—Percocet Post-op: numbness lower left tongue—patient said had to fly to England, against medical advice—developed dry socket and dysthesia Inferior Dental Nerve—treated with Vitamin C 1 gm q.i.d—paste into socket—treated whilst constantly flying in and out of town to South America/Europe—poor compliance, heavy drinking, smoking. Patient got secondary osteomyletis infection from South American trip—after detection of osteomyelitis was placed on Clindamycin told patient had to get serious, stop smoking and drinking, said had to fly to Argentina that night (7 Hours) and to fly back tomorrow (7 hours). Patient improved but lost patient to follow up.

Post-op: Developed Osteomyelitis

Pain Score: 1$^{st}$ Day=1
2$^{nd}$ Day=1

S. Patient 049—26 y/o Male

Problem: trauma case—severe lacerations to lower lip through and through—wound untreated for eight hours post trauma—#24, #25 teeth replaced after being out for one hour although kept moist—high risk of suppuration Procedure—#26 tooth lingually intruded—paste and rinse—high risk of suppuration—area cleaned well with paste and rinse—drain placed into lower lip—teeth washed with rinse—lingual splint to hold teeth in position—also noted green stick fracture of mandible through #19, no treatment—tetanus shot—drain removed next day—paste applied 1) One month later (30 days) teeth #24, 25, 26 root canal treated
2) Lingual splint removed after 21 days—great result, no side effects—no complications Pain Score: 1$^{st}$ Day=0
2$^{nd}$ Day=0

T. Patient 039—30 y/o Male

Problem: #17, #32 very difficult disto-angular large teeth—condylar hyperplasia—difficult extractions—Inferior Dental Nerve involved Procedure—#17, #32 extracted—nerve involvement—left side needed extensive bone removal—Amoxycillin—Ibuprofen 800 mgs—Percocet—Collaplug plus paste Post-op: left side lingual dysthesia with long term discomfort—post-op dry socket—left side irrigated with paste and rinse—Clindamycin 500 mgs t.i.d. for 7 days.

Second procedure—one month later—secondary surgery to remove dead bone fragments, 3 mm×1 mm sitting on nerve—paste and rinse—Clindamycin—follow up visits for paste and rinse—no further problems—lingual dysthesia total improvement Aggregate Pain Score: $1^{st}$ Day=1

$2^{nd}$ Day=1.5

U. Patient 029—96 y/o Male

Problem: #9 needs extracting—poor health—high blood pressure—frail—bone like hard cheese and brittle Procedure—#9 extracted—2 pieces—Straumann implant placed to #9 site BL 4.8×RC 12 mm W/N—freeze dried mineralized bone—rinse after drilling—blood pressure 150/105—control of blood pressure poor did not take medications—good result—no complications Pain Score—$1^{st}$ Day=3, later that day 1

$2^{nd}$ Day=1

V. Patient 032—62 y/o Male

Problem: #13 tooth fractured—close to sinus—tooth had bad smell—allergy to Iodine—

Clindamycin 300 mg t.i.d.×7 days—

Procedure—#13 tooth extracted—rinse to socket—Straumann implant placed to #13 site drilled B/L 4.1×12 mm RC—plus freeze dried mineralized bone—Percocet and Ibuprofen prescribed along with probiotics (jarro-dophilus) and Vitamin C 3 times a day for three weeks—no problems up to and including third day with paste and rinse—no complications Pain Score: $1^{st}$ Day=0

$2^{nd}$ Day=0

W. Patient 036—40 y/o Male

Problem: Severe bruxist—chronic sinusitis—infected tooth #15—Z-Pack—Percocet—Ibuprofen—2 Extra Strength Tylenol Procedure—#15 extracted and implant placed—tooth infected—long term huge sinus communication—irrigated wound and sinus with rinse—Biomend membrane to sinus floor parachute style—freeze dried mineralized bone and CaSo4 primary closure over implant (palatal root)—post op sinus rinse, mouth rinse—no post op problems, says first time that he can remember has not had sinus problems—no complications Pain Score: $1^{st}$ Day=0

$2^{nd}$ Day=0

X. Patient 030—38 y/o Male

Problem: severe caries #9

Procedure—#9 extracted and immediate placement of Straumann implant 4.8×10 mm B/L—Clindamycin—Ibuprofen 800 mgs—freeze dried mineralized bone and paste to wound and socket plus Vitamin E—no complications Pain Score: $1^{st}$ Day=0

$2^{nd}$ Day=0

Y. Patient 031—53 y/o Male

Problem: severe caries #30—Clindamycin 300 mgs t.i.d.×7 days

Procedure—#30 surgical extraction roots—placed Straumann implant to #30 site 4.8×12 mm TE—Percocet—= Vitamin C 500 mgs t.i.d Post-op: side effect to Percocet D/C—used extra strength Tylenol—7 days—may have problems with ibuprofen but took one ibuprofen without problems—alternative days rinse and paste—no complications Pain Score: $1^{st}$ Day=0

$2^{nd}$ Day=0

Z. Patient 028—23 y/o Male

Problem: #30 failed root canal—ETOH alcoholic

Procedure—#30 failed root canal—surgical extraction—Collaplug with paste—no problems post op—wanted more Percocet (addict)—no complications Pain Score: $1^{st}$ Day=1

$2^{nd}$ Day=0

FEMALES×24—Average Age=51.9

AA. Patient 020—23 y/o Female

Problem: very difficult wisdom teeth—mesio angular #17 very close to nerve—deep bony tooth impaction (10/10) high risk—#32 hooked roots Procedure—#1, 16, 17, 32 extractions—#17, #32 Collaplug with paste—#1, #16 paste and irrigation only—also took antibiotics, probiotics—only complication swelling of lower lip—low pain Pain Score: $1^{st}$ Day=0

$2^{nd}$ Day=1

BB. Patient 005—75 y/o Female

Problem: #30 unsalvageable—hyper allergic, 12 medications—allergies to 11 drugs—heavy bruxist—dental phobic—no pain threshold—antidepressants Procedure—#30 immediate extraction mesial root and placement of Straumann implant to #30 site SP 4.8×10 mm W/N Ti—freeze dried mineralized bone—rinse after drilling—paste placed two minutes after surgery—several follow up visits (3)—paste and Vitamin E for 2 minutes—no complications Pain Score: $1^{st}$ Day=3

$2^{nd}$ Day=0

CC. Patient 022—56 y/o Female

Problem: #3 unsalvageable—alcoholic—stopped smoking

Procedure—Multiple surgeries—

1) #3 surgical extraction—socket preservation—rinse after bone removal—freeze dried mineralized bone and CaSo4
2) sinus lift #2, #3—rinse after bone removed—Bio-Oss—placed Straumann implant 4.8×10 mm WN—window covered with Ossix membrane—on antibiotics Augmentin 875 mgs. B.D.
3) #15 sinus lift—Bio-Oss—Bio-Gide-Ossix membrane to furca—rinse after bone removal
4) apicectomy #24, #25—Amoxycillin 500 mgs—freeze dried mineralized bone plus collatape—rinse after bone removal
5) #4 implant placed May 18, 2007 to Mar. 5, 2010 mobile—7 mm bone loss—may have done loading of implant/sinus graft too early—treatment to resuscitate implant—flap, tetracycline 2 minutes—paste 5 minutes—tetracycline rinse—Bio-Oss plus CaSo4 membrane—paste over wound—antibiotics Clindamycin 300 mgs t.i.d.×10 days, Metronidazole 500 mgs.×10 days—rinse daily from May 21, 2010 to Jun. 29, 2010—good result—success—no complications Average Pain Score: $1^{st}$ Day=0

$2^{nd}$ Day=0

DD. Patient 010—47 y/o Female

Problem: severe decay multiple teeth (6)—granulation tissue++++—history of drug abuse and alcohol—no pain threshold Procedure—Multiple extractions—

1) —#14, 15, 17, 18 surgical extractions—Collaplug with paste—post-op—Amoxycillin—Percocet—Ibuprofen 800 mgs.—Vitamin C 500 mgs—minimal pain
2) #3, 5—Clindamycin antibiotic—surgical extraction—patient very agitated—placement of implant into #5 site and removal of granulation tissue with freeze dried mineralized bone, (Bio-Oss or cow bone)—bone also

3 site (Bio-Oss)—then Collaplug with paste and rinse to wound communication into sinus
Pain Score: $1^{st}$ Day=2
$2^{nd}$ Day=0

EE. Patient 006—69 y/o Female
Problem: severe perio disease generally—#31, #32 deep bone loss, mobile teeth—Thyroid disease—Herpes ++++
Pre-op: Clindamycin and Metronidazole—Vallium—Extra-strength Tylenol
First Procedure—#30, #32—surgical extraction—removal of granulation tissue+++++—freeze dried mineralized bone—Collaplug with paste—placement of Straumann implant into #30 site 4.8×10 mm W/N
Post-op: active outbreak of herpes simplex vesicles, Zovirax ointment and Valtrex tablets
Second Procedure—Biopsy upper left soft palate—rinse and paste—Valtrex, Zovirax,
Clindamycin and Metronidazole, for pain Percocet—Vitamin C
Third Procedure—Treatment for severe perio disease
1) deep scale and curettage with irrigation of rinse/paste
2) antibiotics Clindamycin 300 mgs and Metronidazole 500 mgs for 10 days
3) occlusal adjustment
Resounding resolution—pocket depths went from 7 mm and 5 mm to 3 mm with teeth non mobile—no complications
Pain Score: $1^{st}$ Day=0
$2^{nd}$ Day=0

FF. Patient 009—44 y/o Female
Problem: #30 severe pain—flying day after planned surgery
Procedure—#30 extraction with removal of bone—Collaplug with paste—1 Ibuprofen 800 mgs after surgery—2 Percocet 1 before bed—no complications
Pain Score: $1^{st}$ Day=1
$2^{nd}$ Day=0.5

GG. Patient 008—68 y/o Female
Problem: #30 needed extraction—no pain threshold—ETOH—antidepressant—very sensitive tissues—bruxist—reaction to Septocaine—diagnosed with arthritic condition which breaks down bone—Amoxycillin 500 mgs t.i.d.×10 days
Procedure—#30 extracted and immediate 3i implant 5×13 mm placed to #30 site—very brittle++++bone removed—freeze dried mineralized bone—Ossix membrane and CaSo4-Ibuprofen 800 mgs—Tylenol #3 (20)—5 days for pain to decrease—added own mix of colloidal silver and aspirin to wound along with pain killers Tramadol
50 mgs—developed hives with Tramadol pain killer—difficult management case—no complications with surgery
Pain Score: Minimal with pain-killers taken HH. Patient 013—38 y/o Female
Procedure—minor surgery for epulis removal—paste and Vitamin E—no pain, no post op complication "have you done the surgery?"—no complications
Pain Score: $1^{st}$ Day=0
$2^{nd}$ Day=0

II. Patient 015—18 y/o Female
Problem: wisdom teeth extraction 7/10 difficulty—Turner's Syndrome
Procedure—#16, #32 surgical extraction—rinse and paste—antibiotics—no complications
Pain Score: $1^{st}$ Day=0
$2^{nd}$ Day=0

JJ. Patient 014—38 y/o Female
Problem: hyper thyroidism—4 months pregnant—difficult extraction #30 long bulbous roots—2 extra strength Tylenol
Procedure—#30 surgical extraction—socket preservation—freeze dried mineralized bone and CaSo4—great result—no complications
Pain Score: $1^{st}$ Day=0
$2^{nd}$ Day=0

KK. Patient 011—51 y/o Female
Problem: ETOH abuse—drug abuse—epi sensitivity—no pain threshold—12/10 difficulty—high BP—full mouth reconstruction—severe perio disease—high cosmetic case—huge graft dermis Allograft, Emdogain, Miner-Oss bone
First procedure—upper perio flap #2-#6 prep gel and Emdogain to #4 #5. Prepared receptor site #4, sinus elevation TAPP Straumann implant placed to #4 site 4.1×8 mm TE, Allergan over #4 and #5 sites. Facial flap #14, #15 split thickness #12-#13 #14 removed, #12, #13 placed Emdogain—placed Straumann implant to #14 site 4.2×8 mm TE—sinus TAPP Allergan, paste and rinse
Second procedure—Split thickness flap #18-#31, osteotomy site #19, #20, #30 placed Straumann implants to #19, #30 4.8×10 mm W/N and to #20 4.1×10 mm TE, prep gel to #21-#29 Emdogain—bone contouring and Miner-Oss to sockets—limited irrigation of paste
Post-op: patient very difficult management, no compliance and wounds opened up—had to resuture twice, finally placed tape across chin to stop flap being pulled open. Paste was the only salvation—patient returned for rinse and paste Mar. 15, 2011 to Mar. 17, 2011; Mar. 18, 2011-Mar. 21, 2011; Mar. 24, 2011—finally adhesion Apr. 21, 2011
Third procedure—failed implant #14 site, no sinus graft formation, sinus infected, irrigated with rinse—placed Collaplug and paste, freeze dried mineralized bone primary closure—successful graft and new implant site
Fourth procedure—#12 perio breakdown, Tetracyline and paste 2 minutes, Clindamycin. Failed implant #20/21—flap #19 to #23 removed #20 and #21 new Straumann implants 4.1×10 mm, freeze dried mineralized bone plus Biogide—paste applied Aug. 8, 2011, Aug. 11, 2011.
Post-op: lost patient—went to have completion of case elsewhere—last seen area was healing well and surgical sites healed ONLY AS A RESULT OF THE PASTE!!!!!!
Aggregate Pain Score: $1^{st}$ Day=3
$2^{nd}$ Day=2

LL. Patient 021(A)—58 y/o Female
Problem: needs sinus grafts to upper right and upper left sites—high BP—Synthroid for Thyroid—addicted to Nicorette—non stop motion of mouth—labile mood wings
First procedure—sinus grafts upper right #12 position and upper left #14, #15 position—flaps #1-4 and #13-16—Bio-Oss 2 gms—rinse to Osteotemy sites and sinus—Ossix membranes
Second procedure—surgical #2, #14, #15—flaps #1-3, #13-16 Straumann implants placed into #2 site 4.8×10 mm W/N, into #4 site 4.8.×10 mm B/L RC, into #15 site 4.8×10 mm W/N rinse to osteotomy and sinus—good result—no complication
Pain Score: $1^{st}$ Day=1.5
$2^{nd}$ Day=0

MM. Patient 003—86 y/o Female
Problem: tooth #8 tooth avulsed—Clindamycin—long-term severely infected site granulation tissue +++++
Procedure—placement of Straumann implant into #8 site 4.8×12 mm B/L—copious paste and irrigation—no complications
Post-op: Clindamycin caused problem
Pain Score: $1^{st}$ Day=0
$2^{nd}$ Day=0

NN. Patient 019—21 y/o Female

Problem: Extract wisdom teeth (5/10) difficulty
Procedure—#1, #16, #17, #32 surgical extraction—Amoxcillin 500 mgs—Collaplug with paste to lower #17, #32 and rinse to #1, #16—Ibuprofen 800 mgs—Percocet—no complications
  Pain Score: $1^{st}$ Day=2
    $2^{nd}$ Day=1

OO. Patient 023—56 y/o Female
Problem: full mouth reconstruction—thyroid disease—antidepressants—dental phobic
First Procedure—Graft I—periodontal surgery with facial split thickness flap #3-#14—roots had EDTA 17% 2 minutes—Emdogain—Alloderm graft material—paste to wound and flap
Post-op: 1) Flap came loose and re-sutured the next day—paste+irrigation.
2) Flap loose again, re-sutured—paste and rinse—exposed graft material, paste applied to exposed material (Alloderm) #3, 4, 5 region and left on wound for 10 minutes—antibiotics Z-Pack—Ibuprofen 800 mgs—2 days better—flying out of town not good—review when returned after 12 days—paste applied area healing slowly—past and rinse+ Vitamin E
Graft II-#9-#11 position—flying again—die back of flap—paste and rinse and antibiotics—re-closed graft (Alloderm) after wound opened with paste. Complained of pain, tension sutures removed, pain went—good final result—incredible regenerative ability of paste
  Pain Score: $1^{st}$ Day=3
    $2^{nd}$ Day=0

PP. Patient 012—70 y/o Female
Problem: Extract teeth #21, #27—anti depressants—Thyroid disease—high BP—high Cholesterol
Procedure—extracted teeth #21, #27 and immediate placement of Straumann implants to sites #22, #27 4.1×12 mm TE—freeze dried mineralized bone—Collaplug with paste to #24, #25 area—Clindamycin 300 mgs t.i.d.×7 days
Post-op: complained of chest pain—called EMS—EKG normal—heart problems ruled out—said cause of problems gastric reflux from Clindamycin which went away after cessation of
Clindamycin—great result
  Pain Score: $1^{st}$ Day=2
    $2^{nd}$ Day=0

QQ. Patient 007—90 y.o Female
Problem: needed #12, #13 extracted—(sick lady) pace maker—high BP—kidney infection—high cholesterol—thyroid disease—anticoagulant Warfarin—depression
Procedure—#12, #13 surgical extraction—partial loose due to loss of #12, #13—Straumann implant placed to #11 site×10 mm W/N and zest anchors placed to #11 position—freeze dried mineralized bone—rinse and paste applied to wound and implant site—control of PT/PTT—no complications
  Pain Score: $1^{st}$ Day=0
    $2^{nd}$ Day=0

RR. Patient 018—29 y/o Female
Problem: upper wisdom teeth fully erupted 5/10 difficulty—cystic fibrosis
Procedure—#1, #16 surgical extraction—rinse—paste—no complications
  Pain Score: $1^{st}$ Day=0
    $2^{nd}$ Day=0

SS. Patient 017—22 y/o Female
Problem: all wisdom teeth extraction—difficulty 6/10—diabetes insipidous—Ibuprofen 800 mgs—Percocet—Diazepan—2 extra strength Tylenol
Procedure—#1, #16, #17, #32 surgical extraction—paste—rinse—no problems—no complications
  Pain Score: $1^{st}$ Day=1
    $2^{nd}$ Day=1

TT. Patient 016—35 y/o Female
Problem: 3 wisdom teeth need extraction—#1 palatal impaction—#17 100% impacted against #18
Procedure—#1, #17, #32 surgical extraction #17 Collaplug with paste—paste irrigation follow up
Post-op: complained of bad taste and dry socket discovered—pain came from tooth #2 (endodontic abscess) to go to Argentina for root canal and implant
  Pain Score: $1^{st}$ Day=2
    $2^{nd}$ Day=2

UU. Patient 001—46 y/o Female
Problem: multiple extractions—smoker—sugarholic—idiopathic thrombocytopaenia—on prednisone
First procedure—#23, #26, #30 surgical extractions—Collaplug with paste—no complications
Second procedure—#2, #3, #5, #13, #15 surgical extractions—Collaplug with paste—no complications
  Pain Score: $1^{st}$ Day=0
    $2^{nd}$ Day=0

VV. Patient 021(B)—62 y/o Female
Problem: extract all remaining lower teeth
First procedure—#22-#27 surgical extraction placement of implants—8 to lower jaw—4 implants to #18, #19, #20, #21 sites and 4 implants to #37, #28, #29, #30 sites—fractured all rotatory instruments as bone like stone—immediate loading with lower full reconstruction
  Pain Score: $1^{st}$ Day=0
    $2^{nd}$ Day=0
Second procedure—surgery re solitary bone cyst lower left area—cyst size=11.25×18.75—loss of sensation (left inferior dental nerve)—paste and rinse—sensation returned after 3 months
  Pain Score: $1^{st}$ Day=0 (dysthesia)
    $2^{nd}$ Day=0

Summary of Cases by Similar Procedures
24 Female Subjects

| | | | | | | |
|---|---|---|---|---|---|---|
| Extractions Multiple | (001) #23, #26, #30 | | | | | |
| Extractions + Sinus Grafts | (002) #3, #14 | | | | | |
| Extractions + Immediate Implant | (003) #8 | (004) #8, #9 | (005) #30 | (006) #30 | (007) #12 | (008) #30 |
| Extractions + Collaplug + paste + Immediate implant | (009) #30 severe infection | | (010) #14, #15, #17, #18, #31, #32 severe periodontitis | | | |
| Extractions + Immediate Implant + sinus | (011) #4, #14, #19, #30 Emdogain allograft | | (012) #22, #23, #24, #25, #26 #27, #28 implants to | | | |

| | | | | |
|---|---|---|---|---|
| Grafts + alloderm Large soft tissue Grafts | #4-#13, #20-#29 | | sites #22, #27 collaplug + paste to extraction sites | |
| Epulis Removal | (013) #9, #10 region | | | |
| Extractions + Socket Preservation + FDMB + CaSo4 | (014) #30 | | | |
| Extractions Wisdom teeth + paste + rinse | (015) #17, #32 | (016) #1, #32 | (017) #1, #16, #17, #32 | (018) #1, #16 cystic fibrosis |
| Extractions Wisdom teeth + collaplug + paste | (019) #1, #16, #17, #32 | (020) #1, #16, #17, #32 | | |
| Electro-Surgery | (021) upper #6, #11 | | | |
| Implant salvage Tetracycline + Paste + rinse | (022) #4/#5 site implant | | | |
| Allografts & Emdogain | (023) #3-#14, #7 graft Untethered due to talking, re-sutured | | | |
| Trauma lower Lip, tissue tear Thru & thru | (024) | | | |

26 Male Subjects

| | | | | |
|---|---|---|---|---|
| Extractions + Paste + rinse | (025) #15 | (026) #7, #8 | (027) #16 | |
| Extractions + Collaplug + Paste | (028) #30 | | | |
| Extractions + Immediate Implant + Grafting | (029) #9 (034) #19, #20, #28, #30 + bone graft for large cyst | (030) #9 | (031) #30 | (032) #13 (035) #4 + implant #22 + implant | (033) #19, #20, #22 #9 |
| Exractions + Sinus graft + Immediate implant | (036) #15 | (037) #2 | | |
| Extractions Wisdom teeth + rinse + paste | (038) #18 | (039) #17, #32 sequestectomy long healing period (043) #17 osteomyelitis-long recovery, smoker | (040) #1, #16 #17, #32 | (041) #1, #16 #17, #32 (045) #1, #16 #17, #32 | (042) #1, #16 #17, #32 |
| Extractions Wisdom teeth collaplug + paste left in wound | (046) #1, #16, #17, #32 | (047) #1, #16 #17, #32 | | |
| Removal of Tissue, External Resorption + paste | (048) #14 | | | |
| Avulsion of teeth & tissue laceration rinse + paste | (049) #24, #25, #26 tissues of lips, lower jaw | | | |
| Apicectomy + rinse + paste | (050) #8 | | | |
| Cystic #12 & implants | (044) #12, #14 | | | |

Females Pain Scores

| 24 Females-Average Age = 51.9 Average Pain Day 1 = 0.875, Day 2 = 0.3 | | | |
|---|---|---|---|
| | | Record of Pain | |
| No. | Female's Age | Day 1 | Day 2 |
| 001 | 46 | 0 | 0 |
| 002 | 61 | 0 | 0 |
| 003 | 86 | 0 | 0 |
| 004 | 82 | 0 | 0 |
| 005 | 75 | 3 | 0 |
| 006 | 69 | 0 | 0 |
| 007 | 90 | 0 | 0 |
| 008 | 68 | 0 | 0 |
| 009 | 44 | 1 | 0.5 |
| 010 | 47 | 2 | 0 |
| 011 | 51 | 3 | 2 |
| 012 | 70 | 2 | 0 |
| 013 | 38 | 0 | 0 |
| 014 | 38 | 0 | 0 |
| 015 | 18 | 0 | 0 |
| 016 | 35 (pain from abscess on another tooth0 | 2 | 2 |
| 017 | 22 | 1 | 1 |
| 018 | 29 | 0 | 0 |
| 019 | 21 | 1 | |
| 020 | 23 | 1 | |
| 021 | 58 | 0 | |
| 022 | 56 | 0 | |
| 023 | 56 | 0 | |
| 024 | 63 | 0 | |

Pain Scale 0 = None, 1 = Mild, 2 = Moderate, 3 = Extreme

Males Pain Scores

| 26 Males-Average Age = 44.8 Average Pain Day 1 = 0.69, Day 2 = 0.38 | | | |
|---|---|---|---|
| No. | Male's Age | | |
| 025 | 76 | 0.5 | −1 |
| 026 | 79 | 1 | 0 |
| 027 | 35 | 0 | 0 |
| 028 | 23 | 1 | 0 |
| 029 | 96 | 0 | 0 |
| 030 | 38 | 0 | 0 |
| 031 | 53 | 0 | 0 |
| 032 | 62 | 0 | 0 |
| 033 | 90 | 0 | 0 |
| 034 | 47 | 0 | 0 |
| 035 | 80 | 1 | 0 |
| 036 | 40 | 0 | 0 |
| 037 | 70 | 0 | 1 |
| 038 | 47 | 1.5 | 0 |
| 039 | 30 | 1 | 1.5 |
| 040 | 18 | 1.5 | 0 |
| 041 | 19 | 1 | 1 |
| 042 | 15 | 1 | 1 |
| 043 | 49 | 1 | 1 |
| 044 | 17 | 1 | 0 |
| 045 | 19 | 0 | 0 |
| 046 | 18 | 2 | 1.5 |
| 047 | 18 | 2 | 1 |
| 048 | 39 | 1 | 0 |
| 049 | 26 | 0 | 0 |
| 050 | 62 | 0 | 0 |

Results

In the more major surgical cases—extractions and immediate placements of implants, 9 females, 9 males, pain the first day scored on average for males 0.375 Day One and 0.375 Day Two. For females 0.71 Day One and 0.25 Day Two. Only one male patient (90 years of age) complained of pain a 2-3 the first day, 2 the next day but did not take any painkillers and played tennis the next day following three immediate extractions and 3 implant placements.

In the wisdom teeth cases—the more difficult extractions complained of normal swelling post-op. In the rinse/paste cases, 8 males scored with Collaplug 1.3 on Day One and 0.5 Day Two without Collaplug 0.75 on Day One and 0.5 on Day Two. 7 females pain scored with the Collaplug 0.5 on Day One and 0.5 on Day Two and without the Collaplug 0.75 on Day One and 0.2 on Day Two.

One difficult extraction in 1 male, tooth #17, (043) who was also a heavy smoker and two very difficult extractions, teeth #17, #30 (039) developed complications which resulted in second surgical procedures to remove some dead bone and subsequent antibiotic therapy (Clindamycin). They both complained of discomfort that was long term and lasted for three to four weeks. Only one female (016) complained of chronic pain following surgical removal of teeth #1, #32. After further radiographic examination her pain was associated with an abscess in tooth #2, not related to the surgery. She returned to Argentina for removal of the tooth and placement of an implant into the #2 site.

In those patients who had the Collaplug and paste and had all four wisdom teeth removed or had simple extractions plus Collaplug/paste, 3 males, 3 females it was noted a slightly higher pain index in only the males who had the Collaplug when compared to just the rinse and the paste alone. In the females subset there was no difference in pain index between the Collaplug and the rinse and paste. Those patients had virtually no pain at all, score 1 to 2 the first day and only 1 the second day with taking only 1 or 2 Ibuprofen 800 mgs the first day and 1 800 mgs Ibuprofen the second day.

In those cases of sinus grafts or sinus grafts and implants (2 females-002 & 011) (2 males-036 & 037) only one female patient (2 sinus procedures, 1 extraction and 2 immediate implants 011) complained of discomfort post-op. Ranging at the level of 3. In this case (011) Emdogain plus allograph (Alloderm) was placed from #29 to #20 with full surgical mobilization of the upper anterior mucosa, this became un-tethered. The grafts were re-sutured (011) twice without further complications although one implant was lost and re-grafted with minimum pain scored.

A second female patient (023) who also had full arch periodontal grafting from #4 to #20, (Emdogain and allograft (Alloderm)) plus a third patient (002) who had two sinus grafts. The upper anterior mucosa became un-tethered, resulting in one or two more attempts to resuture the mucosa back. All the three female patients had a propensity to talk and the talking had dislodged the sutures. The rinse and paste given daily was the only salvation and allowed all grafts to be salvaged and ended up with very good cosmetic results.

All grafting materials Alloderm, Bio-Guide, Ossix membrane, Bio-Mend, Collatape, Collaplug, Bio-Oss, Miner-Oss, Freeze Dried Bone and implants made by Straumann and 3i were facilitated by the use of the rinse and paste. To the extent that one patient (022) had a loose implant salvaged using Tetracycline etch to clean up the implant surface and the paste used to heal the ailing site. One patient (021B) had eight immediate implants placed plus multiple extractions plus lower immediate full arch reconstruction successfully with little to no pain at all.

An apicectomy on #8 in one male and two cases of trauma involving avulsion of teeth and severe tissue lacerations, one male (049) and one female (024) were treated successfully with the rinse/paste without much surgical pain recorded and great results One case of electrosurgical tissue removed (013) and other minor surgical corrections were conducted using the past/rinse without any post-surgical discomfort.

CONCLUSION

Use of the paste/rinse reduced the occurrence and discomfort of pain dramatically in most surgical patients. The patients who had extractions and were irrigated with the rinse/paste had the least pain of all, as well as the fewest number of complications. The results from this study indicate that the adjunctive use of both the rinse in the wound and the paste post-operatively make a considerable difference to the pain post-operatively and reduced suffrage and post-operative complications to the vast majority of patients. It was noted that the pain killing effect lasted up to two days or 48 hours post placement in the wounds.

What is claimed is:

1. A method for treating a condition comprising administering or applying to a patient a composition comprising:
    a) a chloride salt;
    b) a source of bicarbonate; and
    c) an antimicrobial agent selected from the group consisting of biguanides, bisbiguanides, triguanides and analogs thereof;
    wherein the concentration of the chloride salt in the composition is at least 0.5 M, the concentration of the source of bicarbonate in the composition is at least 4.9 M, and the concentration of the antimicrobial agent is at least 0.5% (w/w);
    wherein the composition is alkaline; and,
    wherein the patient has a condition selected from the group consisting of a wound, a bacterial infection, a viral infection, a fungal infection, inflammation, angiogenesis, and pain.

2. The method of claim 1, wherein the composition comprises a source of hypochlorite at a concentration of at least 0.5% (w/w).

3. The method of claim 1, wherein the chloride salt is selected from the group consisting of sodium chloride and potassium chloride.

4. The method of claim 1, wherein the source of bicarbonate is selected from the group consisting of sodium bicarbonate, calcium bicarbonate, ammonium bicarbonate and sodium percarbonate.

5. The method of claim 2, wherein the source of hypochlorite is N-chloro-tosylamide.

6. The method of claim 1, wherein the antimicrobial agent is chlorhexidine.

7. The method of claim 1, wherein the composition comprises at least one compound selected from the group consisting of a compound that produces oxygen, a poloxamer, a surfactant and a polyhydroxy acid.

8. The method of claim 7, wherein
    the concentration of the oxygen-producing compound in the composition is in the range of about 0.1% (v/v) to about 1% (v/v);
    the concentration of poloxamer in the composition is at least 4% (w/w);
    the concentration of surfactant in the composition is at least about 0.1% (w/w); and,
    the concentration of polyhydroxy acid in the composition is at least about 0.2% (w/w).

9. The method of claim 1, wherein the composition is formulated as a powder, spray, ointment, paste, cream, lotion, gel, solution, patch, or drops.

10. The method of claim 1, wherein the composition is incorporated onto or into a wound dressing material or a plug.

11. The method of claim 1, wherein the composition further comprises a compound selected from the group consisting of an anti-viral compound, an anti-fungal compound and an additional anti-microbial compound.

12. A method for treating a condition, comprising administering to a patient in need thereof a therapeutic composition comprising:
    a) a chloride salt selected from sodium chloride and potassium chloride;
    b) a source of carbonate selected from the group consisting of sodium bicarbonate, potassium bicarbonate, calcium bicarbonate and ammonium bicarbonate;
    c) chlorhexidine;
    d) a source of peroxide selected from hydrogen peroxide, carbamide peroxide and sodium percarbonate;
    e) a poloxamer;
    f) an amphoteric surfactant; and,
    g) a polyhydroxy acid,
    wherein the concentration of the chloride salt in the composition is at least 0.5 M, the concentration of the source of bicarbonate in the composition is at least 4.9 M, and the concentration of the chlorhexidine is at least 0.5% (w/w);
    wherein the composition is alkaline.

13. A method for treating a condition, comprising administering to a patient in need thereof a therapeutic composition comprising:
    a) a chloride salt;
    b) a source of bicarbonate;
    c) an oxygen producing compound;
    d) an antimicrobial agent; and,
    e) a surfactant;
    wherein the concentration of the chloride salt in the composition is in the range of about 4M to about 8M;
    wherein the concentration of the source of bicarbonate is at least 8M; and,
    wherein the composition is alkaline.

14. The method of claim 12, wherein the concentration of the source of peroxide is in the range of about 0.1% (v/v) to about 1% (v/v);
    the concentration of the poloxamer in the composition is at least 4% (w/w);
    the concentration of the amphoteric surfactant in the composition is at least about 0.1% (w/w); and,
    the concentration of polyhydroxy acid in the composition is at least about 0.2% (w/w).

15. The method of claim 12, wherein the poloxamer comprises poloxamer 237, the amphoteric surfactant comprises lauramine oxide, and the polyhydroxy acid comprises gluconolactone.

16. The method of claim 13, wherein the concentration of the oxygen-producing compound is in the range of from about 0.11% (v/v) to about 1% (v/v), and wherein the concentration of the antimicrobial agent is in the range of from about 0.5% (w/w) to about 5% (w/w).

17. The method of claim 13, wherein the composition comprises a source of hypochlorite at a concentration of at least 0.5% (w/v).

18. The method of claim 13, wherein the composition further comprises at least one compound selected from the group consisting of a poloxamer, a surfactant and a polyhydroxy acid.

19. The method of claim 18, wherein
- the concentration of poloxamer in the composition is at least about 6% (w/v);
- the concentration of surfactant in the composition is at least about 0.1% (w/v);
- the concentration of polyhydroxy acid in the composition is at least about 0.2% (w/v).

* * * * *